United States Patent [19]

Annis et al.

[11] Patent Number: 6,063,932
[45] Date of Patent: May 16, 2000

[54] PROCESS AND INTERMEDIATES FOR THE PREPARATION OF OXAZOLINE DERIVATIVES

[75] Inventors: Gary David Annis, Landenberg, Pa.; Rafael Shapiro, Wilmington, Del.

[73] Assignee: E. I. du Pont de Nemours and Company, Wilmington, Del.

[21] Appl. No.: 09/308,128

[22] PCT Filed: Nov. 13, 1997

[86] PCT No.: PCT/US97/20798

§ 371 Date: May 13, 1999

§ 102(e) Date: May 13, 1999

[87] PCT Pub. No.: WO98/22448

PCT Pub. Date: May 28, 1998

[51] Int. Cl.[7] .................. C07D 263/10; C07C 233/64; C07C 233/68; C07C 317/14
[52] U.S. Cl. .................. 548/237; 564/158; 564/161; 564/337; 568/31; 568/32
[58] Field of Search ................ 548/237; 564/158, 564/161, 337; 568/31, 32

[56] References Cited

U.S. PATENT DOCUMENTS 5,354,905  10/1994  Sato et al. ........................... 564/186

FOREIGN PATENT DOCUMENTS 0 594 179  4/1994  European Pat. Off. .

WO 96/11190  4/1996  WIPO .
97/26249  7/1997  WIPO .

OTHER PUBLICATIONS

Lusskin, Robert M. et al., A New Reaction of Nitriles. V. Preparation of N–(2–Halo–1–ethyl)–amides, *Journal of The American Chemical Society*, 72, 5577–5578, Dec. 1950.

Christol, Henri et al., Transpositions acidocatalysées (X$^e$ memoire). Reaction de Ritter sur les alcools benzyliques secondaires et les benzylcarbinols, *Bulletin de la Societe Chimique de France*, 8, 2313–2318, 1961.

*Primary Examiner*—Fiona T. Powers

[57] ABSTRACT

Arthropodicidal oxazoline derivatives and processes and intermediates for the preparation thereof are disclosed. The intermediates are racemic or enantiomerically enriched compounds having formula (I), wherein R and n are disclosed in the specification.

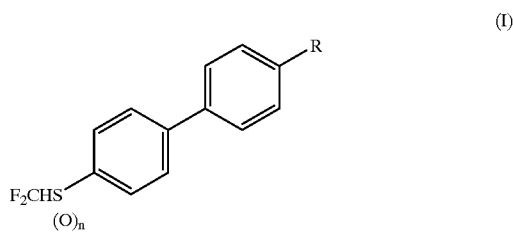

11 Claims, No Drawings

PROCESS AND INTERMEDIATES FOR THE PREPARATION OF OXAZOLINE DERIVATIVES

CROSS REFERENCE TO RELATED APPLICATION

This application was filed under 35 U.S.C. 371 from international application no. PCT/US97/20798, internationally filed Nov. 13, 1997 which claims priority benefit from provisional application no. 60/031,068, filed Nov. 18, 1996 and provisional application no. 60/040,479, filed Mar. 12, 1997.

FIELD OF THE INVENTION

The present invention relates to arthropodicidal oxazolines and processes and intermediates for the preparation thereof.

BACKGROUND OF THE INVENTION

The present invention relates to the preparation of novel intermediates and particular oxazolines which are known to have arthropodicidal activity. Although WO 96/11190, EP 594179-A1 and U.S. Pat. No. 5,354,905 disclose methodologies for oxazoline preparation, the present invention provides a potential commercial preparation of these particular oxazolines which has been limited because previous preparations were too expensive or complicated. There is a continuing need to discover new processes for the preparation of oxazolines where the preparation offers distinct advantages that add to their desirability. The processes of the present invention provide novel and direct routes typically using well-known and commercially available starting materials.

SUMMARY OF THE INVENTION

The present invention pertains to novel compounds having Formula I and processes for the preparation thereof:

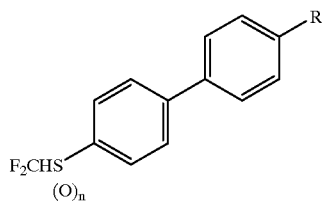

wherein
R is selected from H, —C(O)CH$_2$R$^4$, —CH(OH)CH$_2$R$^4$, —CH(NH$_2$)CH$_2$R$^4$ and

and salts thereof;
R$^4$ is OC(O)Ar, Cl, or Br;
R$^5$ is OH, Cl, Br, or OSO$_2$A;
A is methyl, phenyl or p-tolyl;
Ar is 2,6-difluorophenyl, 2-chlorophenyl or 2-chloro-6-fluorophenyl;
n is 1 or 2; and
*denotes a stereogenic center.

The present invention further pertains to compounds of Formula I wherein R is:

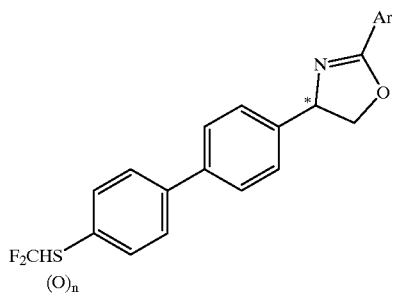

and a composition comprising a mixture of compounds of Formula I, having the stereogenic center designated by *, which compounds are enantiomerically enriched in the S configuration.

This invention further pertains to a process for preparing a racemic or enantiomerically enriched arthropodicidal oxazoline of Formula II:

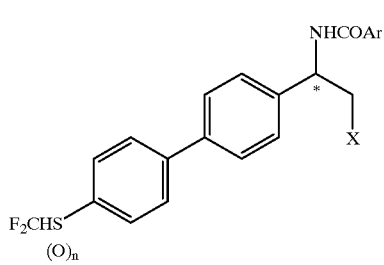

wherein

Ar is 2,6-difluorophenyl, 2-chlorophenyl or 2-chloro-6-fluorophenyl;

n is 1 or 2; and

*denotes a stereogenic center;

comprising cyclizing a compound of Formula III:

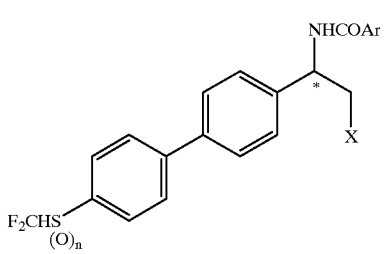

wherein

X is Cl, Br or OSO$_2$A;

A is methyl, phenyl or p-tolyl.

The present invention further pertains to a process comprising the additional step of preparing a compound of Formula III by reacting a compound of Formula IV:

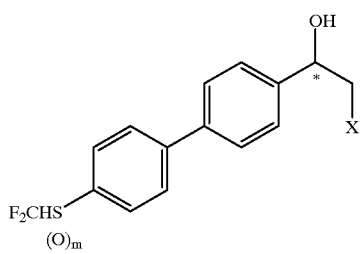

IV where m is 0, 1 or 2 with ArCN provided that when m is 0 an oxidation is performed to provide the compounds where n is 1 or 2, and a process comprising the additional step of preparing the compound of Formula V:

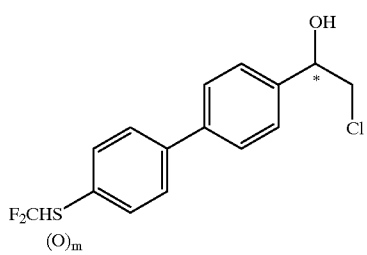

V by reducing a compound of Formula VI:

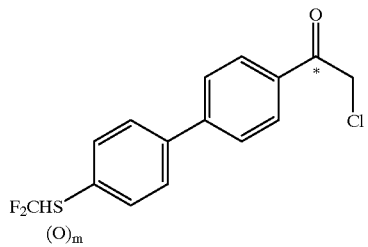

VI and a process comprising the additional step of preparing the compound of Formula VI wherein m is 1 or 2, by reacting a compound of Formula VII:

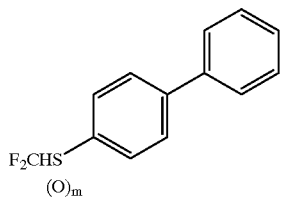

VII with $ClCH_2C(O)Cl$ in the presence of aluminum trichyloride.

The present invention further pertains to a process comprising the additional step of preparing a compound of Formula III wherein X is Cl, comprising reacting a compound of Formula VII with a compound selected from compounds of the formula $ArC(O)NHCH=CHCl$, $ArC(O)NHCHOHCH_2Cl$ and $ArC(O)NHCH(CH_2Cl)OCH(CH_2Cl)NHC(O)Ar$ and mixtures thereof.

The present invention further pertains to a compound having the formula selected from $ArC(O)NHCH=CHCl$, $ArC(O)NHCHOHCH_2Cl$ and $ArC(O)NHCH(CH_2Cl)OCH(CH_2Cl)NHC(O)Ar$ wherein Ar is 2,6-difluorophenyl, 2-chlorophenyl or 2-chloro-6-fluorophenyl, and particularly a compound having Formula VIII:

$$ArC(O)NHCH(CH_2Cl)OCH(CH_2Cl)NHC(O)Ar \quad \text{VIII}$$

wherein Ar is 2,6-difluorophenyl as well as a process for preparing a compound of Formula VIII by reaction of an amide of Formula IX:

$$Ar\ CONH_2 \quad \text{IX}$$

with chloroacetaldehyde in the presence of a catalyst in a solvent

DETAILS OF THE INVENTION

The present invention includes novel processes illustrated by Schemes A1, A2, A3, B1, B2, B3, C1, C2 and C3 for preparing compounds of Formula 1 (including compounds of Formula II) and key intermediates leading thereto which are racemic or enantiomerically-enriched at the stereogenic center indicated by the asterisk.

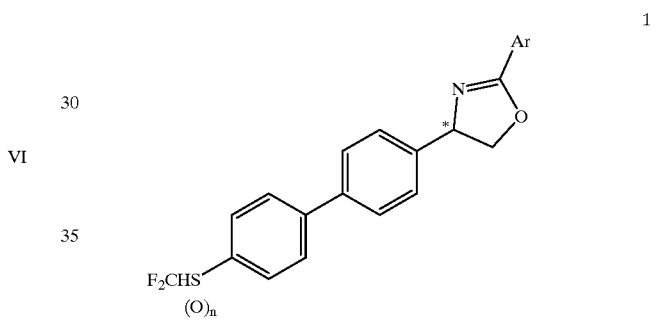

1 wherein n is 0, 1 or 2; and

Ar is 2,6-difluorophenyl, 2-chlorophenyl or 2-chloro-6-fluorophenyl.

The asterisk used in chemical structures throughout this disclosure identify stereogenic centers, [H] indicates reductions, and [O] indicates oxidations.

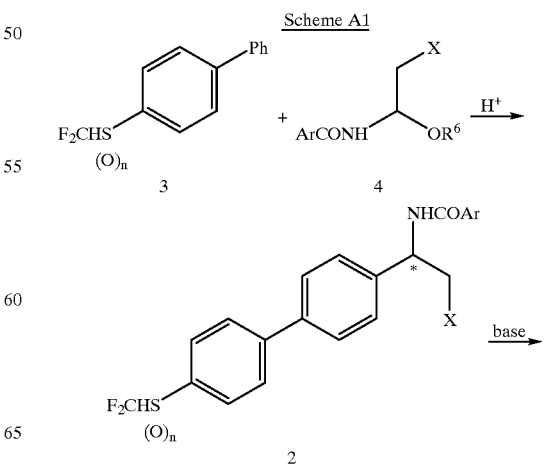

5
-continued

[Structure 1: biphenyl with oxazoline bearing Ar group and F₂CHS(O)ₙ substituent]

wherein n is 1 or 2;

X is Cl, Br or OSO₂A;

A is methyl, phenyl or p-tolyl;

$R^6$ is H or CH(CH₂X)NHC(O)Ar; and

Ar is 2,6-difluorophenyl, 2-chlorophenyl or 2-chloro-6-fluorophenyl.

Scheme A2

[Structure: 3 + XCH₂C(O)X with AlCl₃ → biphenyl ketone 5 with F₂CHS(O)ₙ; then 1. [H] 2. ArCN / H⁺ → 2; then base → 1]

wherein n is 1 or 2;

X is Cl or Br; and

Ar is 2,6-difuorophenyl, 2-chlorophenyl or 2-chloro-6-fluorophenyl.

Scheme A3

5 →(1. asymm [H], 2. MeSO₂Cl)→ 6 [Structure with OSO₂Me, X, F₂CHS(O)ₙ] →(1. NaN₃, 2. [H], 3. ArCOCl)→

6
-continued

[Structure 2(S enantiomer): biphenyl with NHCOAr, X substituents and F₂CHS(O)ₙ]

wherein n is 1 or 2;

X is Cl or Br; and

Ar is 2,6-difluorophenyl, 2-chlorophenyl or 2-chloro-6-fluorophenyl.

Scheme B1

[Structure 7: R¹C(O)S-C₆H₄-Ph] →(1. AcCl/AlCl₃, 2. HOCH₂CH₂OH/H⁺, 3. NaOH)→

[Structure 8: biphenyl with dioxolane-methyl group and HS] →(1. ClCHF₂/NaOH, 2. Halogenation, 3. H₃O⁺)→

5 (n is 0) →(as in A2 or A3)→ 1 (n is 0) →[O]→ 1 (n is 1) →[O]→ 1 (n is 2)

wherein

R¹ is N(CH₃)₂ or OR²;

$R^2$ is $C_1$ to $C_4$ alkyl;

X is Cl or Br; and

Ar is 2,6-difluorophenyl, 2-chlorophenyl or 2-chloro-6-fluorophenyl.

Scheme B2

[Structure: Br-C₆H₄-Ph] →(1. AcCl/AlCl₃, 2. HOCH₂CH₂OH/H⁺, 3. 3 NaSMe)→ 8 →(as in B1)→ 1 wherein n is 0, 1 or 2;

X is Cl or Br; and

Ar is 2,6-difluorophenyl, 2-chlorophenyl or 2-chloro-6-fluorophenyl.

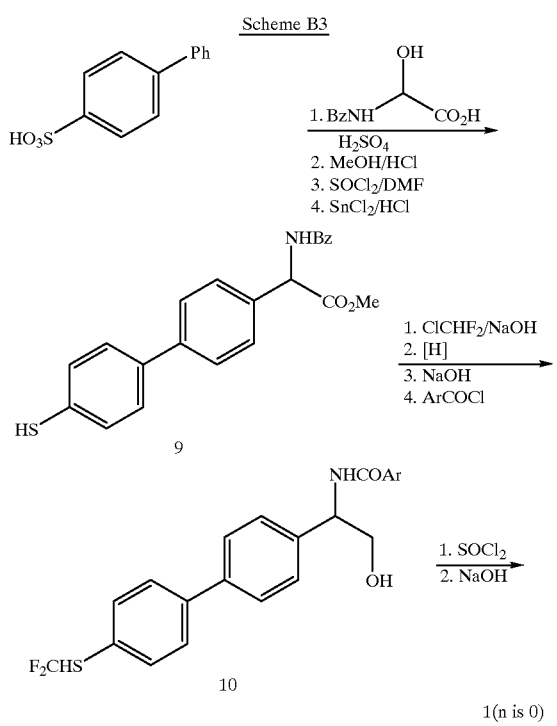

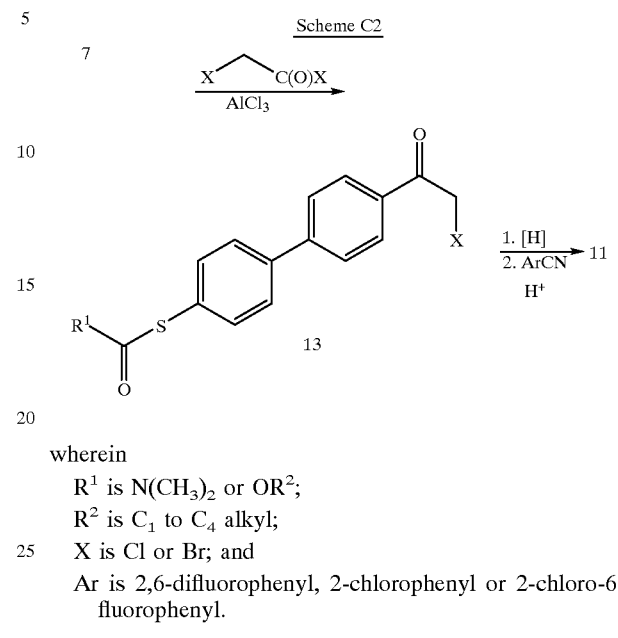

X is Cl or Br; and
Ar is 2,6-difluorophenyl, 2-chlorophenyl or 2-chloro-6-fluorophenyl.

wherein
R$^1$ is N(CH$_3$)$_2$ or OR$^2$;
R$^2$ is C$_1$ to C$_4$ alkyl;
X is Cl or Br; and
Ar is 2,6-difluorophenyl, 2-chlorophenyl or 2-chloro-6-fluorophenyl.

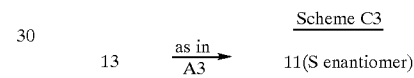

wherein
R$^1$ is N(CH$_3$)$_2$ or OR$^2$;
R$^2$ is C$_1$ to C$_4$ alkyl;
X is Cl or Br; and
Ar is 2,6-difluorophenyl, 2-chlorophenyl or 2-chloro-6-fluorophenyl.

In Schemes A1–A3, the oxidized compounds of Formula 1 (n is 1 or 2) are prepared from 4-[(difluoromethyl)sulfinyl]- or 4-[(difluoromethyl)sulfonyl]biphenyl by the methods of Schemes A1, A2 or A3 via amides of Formula 2 (including compounds of Formulas I and III). In Schemes B1–B3, a sulfur-derivative of biphenyl is transformed via similar methods to a thiol of Formula 8 or 9, which can then be converted into compounds of Formula 1 corresponding to either sulfide 1 (n is 0), sulfoxide 1 (n is 1), or sulfone 1 (n is 2). In Schemes C1–C3, the compounds of Formula 1 (n is 0) may also be prepared from derivatives of biphenylthiol of Formula 7 via S-protected compounds of Formula 11, which are further processed by cyclization, deprotection, and difluoromethylation.

The processes of Schemes A1–C3 provide particularly valued intermediates such as the racemic or enantiomerically-enriched compounds having the formula:

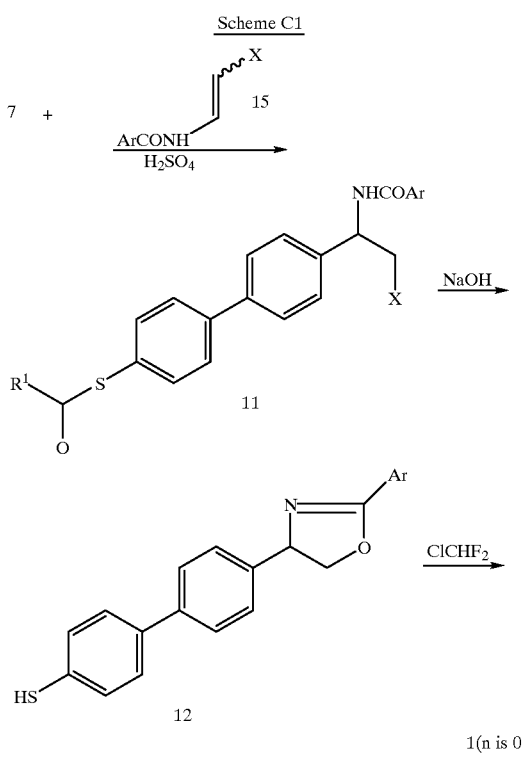

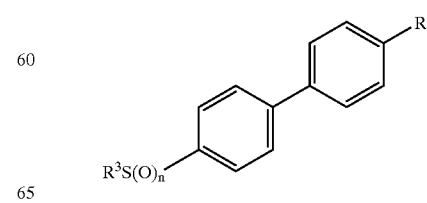

wherein

R is selected from

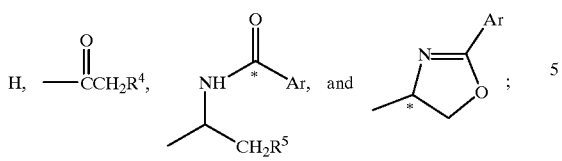

Ar is 2,6-difluorophenyl, 2-chlorophenyl or 2-chloro-6-fluorophenyl;

$R^3$ is H, $COR^1$, or $CHF_2$;

$R^1$ is $N(CH_3)_2$ or $OR^2$;

$R^2$ is $C_1$ to $C_4$ alkyl;

$R^4$ is Cl, or Br.

$R^5$ is OH, Cl, Br, or $OSO_2A$, where A is $CH_3$, phenyl, or p-tolyl; and n is 0, 1 or 2; and

*denotes a stereogenic center; provided that:
when $R^3$ is $COR^1$, then n is 0;
when R and $R^3$ are H, then n is 2; and
when R is H, then $R^1$ is other than $N(CH_3)_2$, which are especially useful for preparing racemic or non-racemic arthropodicidal oxazolines of Formula 1. Of particular note for reasons of economy are the processes of Schemes A1 and A2, wherein n is 2 and Ar is 2,6-difluorophenyl. For reasons of increased arthropodicidal activity, compositions of Formula 1 with at least 20% enrichment of the S enantiomer and precursors which lead to the S enantiomer of Formula 1 are preferred.

The methods of Schemes A1–A3 are outlined in Equations 1–13.

The compounds of Formula 1 are prepared by the cyclization of amides of Formula 2 as shown in Equation 1 by contacting with 0.9 to 2 equivalents of a strong base, such as an alkali-metal hydroxide, either as a solution in a solvent such as a lower alcohol, or in a water-immiscible solvent such as toluene or dichloromethane, in the presence of a phase-transfer catalyst, such as a quaternary-ammonium halide. The reaction is typically conducted at 5 to 35° C. for 0.5 to 6 h, and the product is isolated by dilution with water, concentration, and filtration.

Equation 1

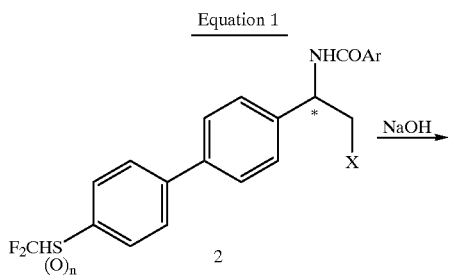

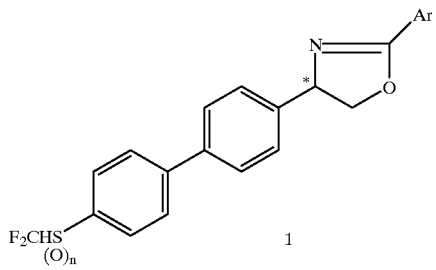

wherein n is 0, 1, or 2;

Ar is 2,6-difluorophenyl, 2-chlorophenyl, or 2-chloro-6-fluorophenyl; and

X is Cl, or Br, or $OSO_2A$, where A is $CH_3$, phenyl, or p-tolyl.

The compounds of Formula 2 are prepared as shown in Equation 2 by the condensation of a compound of Formula 3 (which is included in compounds of Formula I and includes compounds of Formula VII) with a compound of Formula 4 (including compounds of Formula VIII) or Formula 15 or mixtures thereof. The reaction is catalyzed by a suitable acid or Lewis acid such as, but not limited to, sulfuric, phosphoric, or hydrofluoric acid, optionally in the presence of an inert diluent, such as, but not limited to, dichloromethane, 1,2-dichloroethane, or acetic acid. The reaction is typically conducted between –10 to 100° C. with 0 to 25° C. being preferred. The product is isolated by dilution with water and filtration.

Equation 2

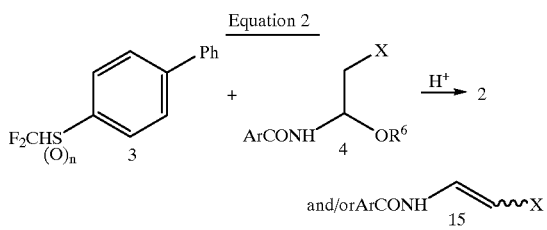

wherein n is 1 or 2;

Ar is as defined for Equation 1; and

X is Cl or Br.

$R^6$ is H or $CH(CH_2X)NHC(O)Ar$

Compounds of Formula 4 are prepared by reaction of aryl amides of Formula 14 with a haloacetaldehyde in the presence of a Lewis acid or acid catalyst such as, but not limited to methanesulfonic acid, p-toluenesulfonic acid, sulphuric acid, or hydrogen chloride.

The reaction is conducted in a suitable organic solvent such as, but not limited to dichloromethane, butyl chloride, 1,2-dichloroethane or toluene at 38–100° C., with temperatures of 40–45° C. being preferred. Water may be removed from the chloroacetaldehyde initially by suitable means, or azeotropically as the reaction is conducted. Removal of water from the reaction mixture, by azeotrope for example, is necessary to drive the reaction to completion. The boiling point of the mixture may be adjusted by application of vacuum when necessary. Selective isolation by filtration of the compounds of Formula 4 is possible when the appropriate solvent is used. Equation 3 illustrates this transformation.

Increased reaction times affords mixtures of compounds of Formula 4 and Formula 15. Compounds of Formula 4 where $R^6$ is lower alkyl are described in U.S. Pat. No. 5,354,905.

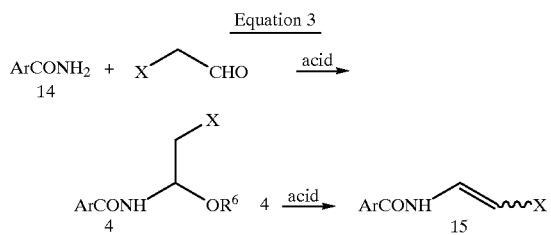

Equation 3 wherein
Ar is as defined for Equation 1;
X is Cl or Br; and
$R^6$ is H or $CH(CH_2X)NHC(O)Ar$.

The biphenyl sulfone of Formula 3 (n is 2) is prepared as shown in Equation 4 by oxidation of the corresponding sulfide 3 (n is 0) with 2.0 to 3.0 oxygen equivalents of an oxidant, such as, but not limited to, peracetic acid or hydrogen peroxide. It is advantageous to use a catalyst, such as a strong acid or a tungstate, molybdate, or vanadate salt with the latter reagent, and to operate the process in a solvent such as acetic acid. The process is typically carried out by adding 2.5 equivalents of 30% aqueous hydrogen peroxide to a solution of 3 (n is 0) and 4 to 8 parts of acetic acid containing 2 to 6 mol % of sodium tungstate at between 50 and 100° C., preferably between 65 and 75° C. over 0.5 to 5 h. The product is isolated by dilution with water and filtration. It is obvious to one skilled in the art that the corresponding sulfoxide of Formula 3 (n is 1) is easily prepared by any of a large number of standard oxidation methods, for example, those cited in J. March, *Advanced Organic Chemistry, Reactions, Mechanisms, and Structure*, 4th edition, J. Wiley & Sons, New York, p. 1202.

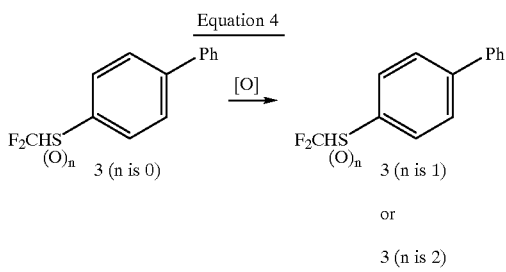

Equation 4

The sulfide of Formula 3 (n is 0) is prepared by the reaction of 4-biphenylthiol with 1 to 3 equivalents of chlorodifluoromethane by the method shown in Equation 5, using 0.9 to 2.0 equivalents of a base, such as, but not limited to, sodium hydroxide in a solvent such as dioxane or N,N-dimethylacetamide. The product is isolated by dilution with water and filtration.

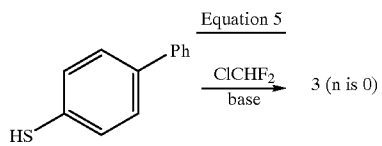

Equation 5

An alternative synthesis of compounds of Formula 2 involves the Ritter reaction of a halohydrin of Formula 16 (which are included in compounds of Formulas I and IV and include compounds of Formula V) or olefin of Formula 17 with the appropriate benzonitrile of Formula 18, as shown in Equation 6. The reaction is conducted by contacting the reactants with a strong acid, such as sulfuric or methanesulfonic, optionally with an inert diluent, such as dichloromethane or 1,2-dichloroethane. When the halohydrin is the reactant, the olefin is an intermediate in the process. The product is isolated by dilution with water and crystallization with a solvent, such as hexane. Alternatively, the product is extracted with an organic solvent and carried forward for further processing.

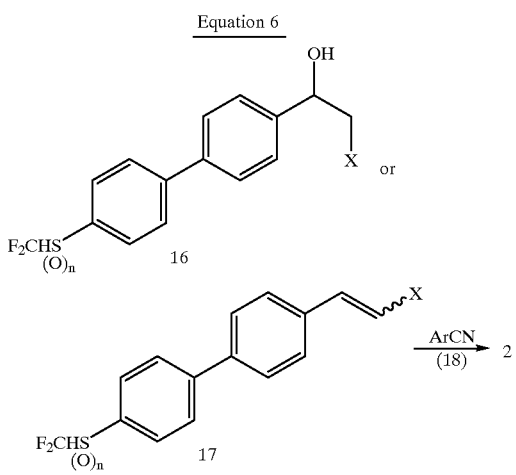

Equation 6 wherein
n is 0 1,or 2;
Ar is as defined for Equation 1; and
X is Cl, Br, or $OSO_2A$, where A is $CH_3$, phenyl or p-tolyl.

The halohydrins of Formula 16 are prepared as shown in Equation 7 from the corresponding phenacyl halides of Formula 5 (which are included in compounds of Formula I, and include compounds of Formula VI) with a reducing agent such as, but not limited to, diborane or sodium borohydride. The latter reagent is preferred for reasons of economy and is typically conducted in an aqueous organic medium, such as aqueous tetrahydrofuran with 0.2 to 0.6, preferably 0.35, molar equivalents of sodium borohydride, between 0 to 35° C., preferably at 10° C., at a pH value between 7 and 11. The product is generally isolated by dilution with water or dilute aqueous acid, concentration, and filtration.

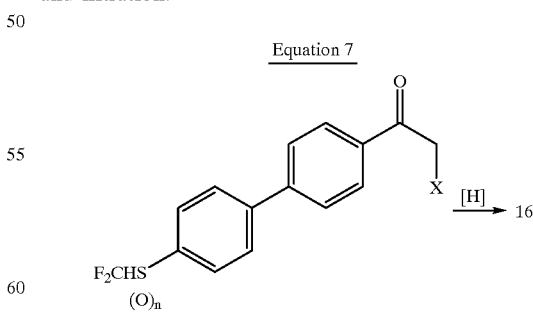

Equation 7 wherein
n and X are as defined in Equation 6.

The phenacyl halides of Formula 5 are prepared as shown in Equation 8 by the Friedel-Crafts reaction of biphenyl derivatives of Formula 3 with 0.9 to 1.5 equivalents of a haloacetyl halide or anhydride, such as chloroacetyl chloride, and 1.8 to 2.5 molar equivalents of a powerful acylation catalyst, such as aluminum trichloride, preferably in an inert solvent, such as dichloromethane or 1,2-dichloroethane. The reaction is typically conducted by adding the reactants together in solution to a slurry of the aluminum trichloride between −5 and 60° C. preferably at 25° C., allowing them to react for 0.5 to 15 h and quenching the mixture with ice. The product is isolated by concentration and filtration and is purified to remove unwanted isomers by recrystallization from or washing with a suitable solvent, such as isopropanol.

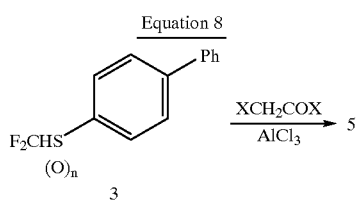

wherein n is 1 or 2; and

X is Cl or Br.

The nonracemic versions of compounds of Formula 1 are advantageously prepared as outlined in Equation 9 by the reaction of a nonracemic amine salt of Formula 19 with approximately one equivalent of the appropriate aroyl chloride of Formula 20 in a water-immiscible organic solvent in the presence of 2 to 2.5 equivalents of an aqueous base, such as sodium hydroxide, in a manner well-known to one skilled in the art. The intermediate products of Formula 2 are isolated by concentration and crystallization and converted to compounds of Formula I in the manner outlined in Equation 1. Alternatively, an additional 0.5–3 equivalents of the base are added to the reaction mixture, along with a suitable phase-transfer catalyst, to provide the compounds of Formula 1 more directly.

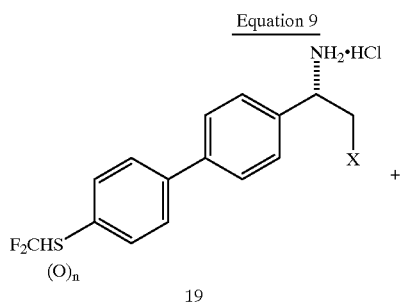

wherein n, Ar and X are as defined in Equation 6.

The nonracemic compounds of Formula 19 (which is included in compounds of Formula I) are prepared as shown in Equation 10 from nonracemic azides of Formula 21 by catalytic hydrogenation or other methods well known in the art (e.g., reaction with trimethyl phosphite, followed by hydrolysis: A. Zidani et al., *Bull. Chem. Soc. Fr.* 1992, 129, 71). Typically, the compound of Formula 21 is contacted with hydrogen gas over a noble metal catalyst, such as Pt, or Pd in a solvent such as methanol containing 0.9 to 3 equivalents of an acid, such as HCl, the catalyst is filtered, and the solvent is removed to provide the amino-chloride of Formula 19 as its hydrochloride salt.

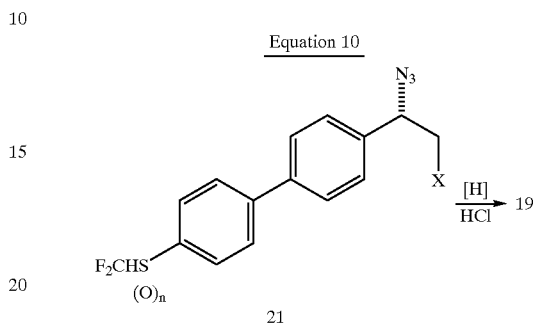

wherein n and X are as defined in Equation 6.

The nonracemic azides of Formula 21 are prepared as shown in Equation 11 by contacting nonracemic methanesulfonates of Formula 6 (which is included in compounds of Formula I) with 0.9 to 3 equivalents of a salt of hydrazoic acid, such as sodium azide, preferably in a polar organic solvent such as N-methylpyrrolidinone, at between 5 and 50° C. The product, which consists predominantly of the (S)-enantiomer, arising from the (R)-configured precursor, is isolated by dilution with water and filtration or extraction.

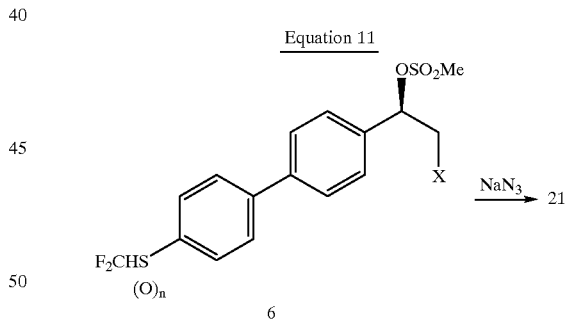

wherein n and X are as defined in Equation 6.

The nonracemic methanesulfonates of Formula 6 are prepared as shown in Equation 12 from nonracemic halohydrins of Formula 16 (R enantiomer) by contacting the latter with 1.0 to 2.0 equivalents of a methanesulfonyl halide or anhydride with 1 to 10 equivalents of an acid-binding agent, such as pyridine, optionally in an inert solvent such as dichloromethane. Preferably, the reaction is carried out in pyridine as a solvent at between −10 and 35° C. and the product is isolated by dilution with water and filtration.

Equation 12

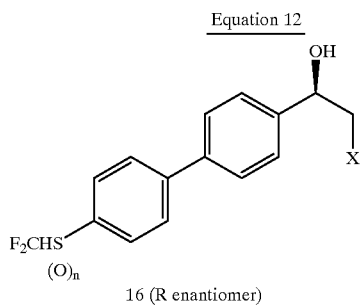

16 (R enantiomer)

wherein n and X are as defined in Equation 6.

The nonracemic halohydrins of Formula 16 (R enantiomer) are prepared as shown in Equation 13 from phenacyl chlorides of Formula 5 by contacting the latter in a suitable solvent, such as tetrahydrofuran, with 0.3 to 1 molar equivalents of a borane reducing agent, such as borane-dimethyl sulfide complex, in the presence of an optically-active amino-alcohol, such as [S-(R*,S*)]-2-amino-1,2-diphenylethanol (alternatively named (1S, 2R)-2-amino-1,2-diphenylethanol) according to methods well-known in the art (e.g., G. Quallich and T. M. Woodall, Synlett. 1993, 929). The product, which consists predominantly of the (R)-enantiomer, is isolated by dilution with aqueous acid, concentration, and filtration.

Equation 13

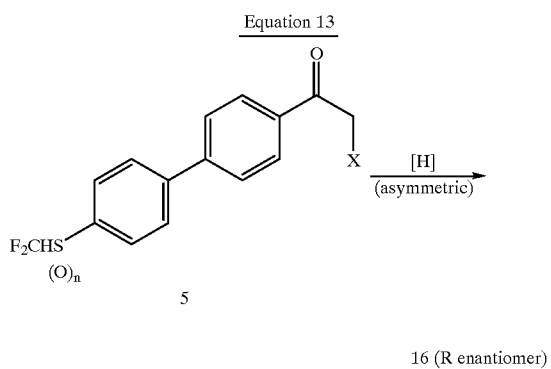

16 (R enantiomer)

wherein n and X are as defined in Equation 6.

The methods of Schemes B1–B3 are outlined in Equations 14–26.

The phenacyl halides of Formula 5 are prepared as shown in Equation 14 by halogenation of ketals of Formula 22 with reagents such as, but not limited to, bromine or sulfuryl chloride, followed by hydrolysis with aqueous acid. The first reaction is typically conducted in an anhydrous inert solvent such as dichloromethane, or tetrahydrofuran, and the halogenating agent (0.9 to 1.2 equivalents) is introduced at between −10 and 35° C. The intermediate haloketal is isolated or, alternatively, water or aqueous HCl, HBr, or sulfuric acid, is added to the reaction mixture, which is then heated at between 40 and 100° C. to hydrolyze the ketal group. The product is isolated by concentration and filtration and is purified by recrystallization from a suitable solvent, such as isopropanol.

Equation 14

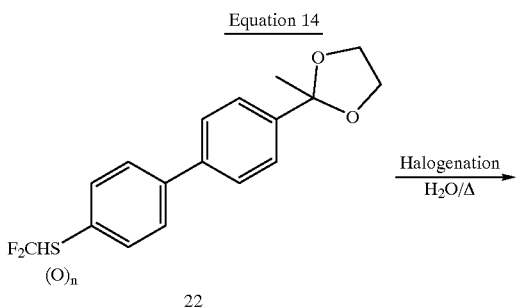

wherein n is 0, 1 or 2, and

X is Cl or Br.

Compound 22 (n is 0) is prepared as shown in Equation 15 by the difluoromethylation of Compound 8 by the method described for Equation 5. Compound 8 is prepared from compounds of Formula 7 by acetylation with acetyl chloride and aluminum trichloride analogous to the procedure described for Equation 8, followed by ketalization and saponification procedures well-known to those skilled in the art. The starting materials of Formula 7 ($R^1$ is $OR_2$) may be prepared by the reaction of biphenyl-4-thiol with alkyl chloroformates by procedures well-known to one skilled in the art. The compound of Formula 7 ($R^1$ is $NMe_2$) has been prepared from biphenyl4-ol by Newman-Kwart rearrangement (J. Chem. Soc., Perkin I, 1987, 187). Compounds of Formulas 22 (n is 1) or 22 (n is 2) are prepared by oxidation methods well-known to those skilled in the art, e.g., buffered peracetic acid, or $NaOCl/RuCl_3$.

Equation 15

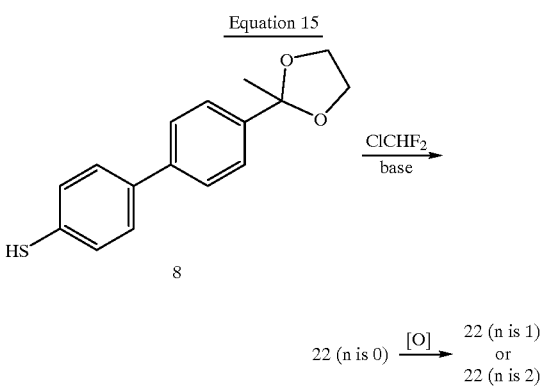

-continued

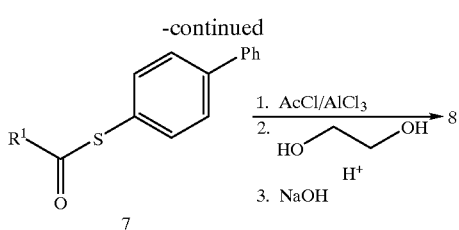

wherein

R$^1$ is N(CH$_3$)$_2$ or OR$^2$; and
R$^2$ is C$_1$–C$_4$ alkyl.

Alternatively, Compound 8 is prepared as shown in Equation 16 by thiolation of Compound 23 (*J. Am Chem. Soc.* 1988, 110,4197) by procedures well-known to those skilled in the art.

Equation 16

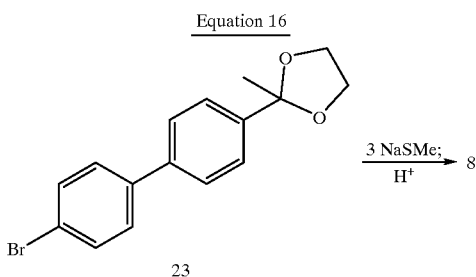

Compounds of Formula 2 are also prepared as shown in Equation 17 by the reaction of hydroxyamides of Formula 24 (which is included in compounds of Formula I) with a reagent such as phosphorus oxychloride, phosphorus tribromide, or thionyl chloride. The reaction is generally carried out in the reagent as solvent or advantageously in an inert diluent, such as dichloromethane, at between –5 and 40° C. and the product is isolated by concentration to dryness, or dilution with water, concentration, and filtration.

Equation 17

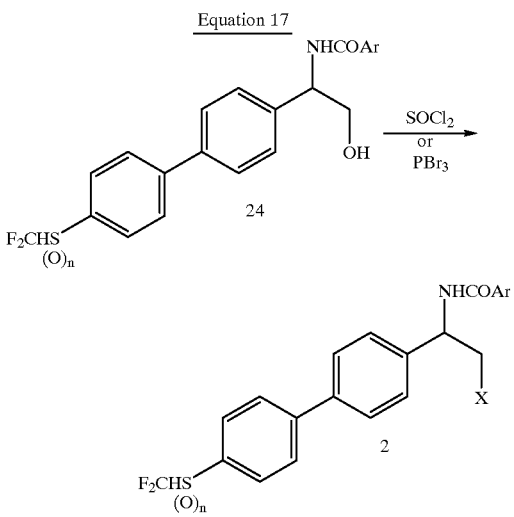

wherein n is 0, 1, or 2;
Ar is as defined for Equation 1; and
X is Br or Cl.

The compounds of Formula 24 are prepared as shown in Equation 18 by reduction of compounds of Formula 25 using a suitable reagent such as lithium borohydride, calcium borohydride, and the like in a suitable organic solvent such as, but not limited to, ether, tetrahydrofuran, or ethanol. The reaction is usually conducted between 0 and 100° C. For carboxylic acids of Formula 25, where R$^7$ is H, a suitable catalyst such as iodine is used (*J. Org. Chem.* 1993, 58, 3568). The esters of Formula 25, where R$^7$ is lower alkyl, are prepared from the corresponding acids by esterification methods well-known to one skilled in the art.

Equation 18

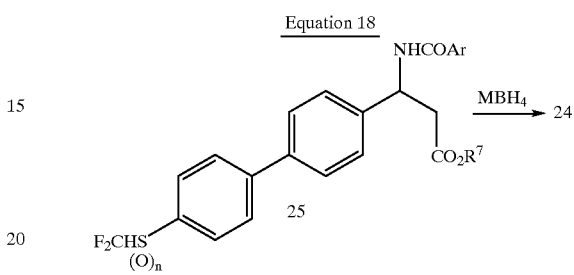

wherein n is 0, 1, or 2;
R$^7$ is H or R$^2$;
R$^2$ is C$_1$–C$_4$ alkyl;
Ar is as defined for Equation 1; and
M is Li, Ca, etc.

The carboxylic acids of Formula 25 are prepared from compounds of Formula 3 and α-hydroxy-hippuric acid derivatives of Formula 26 by the reaction shown in Equation 19, which is carried out in strict analogy with the reaction of Equation 2. When making compounds of Formula 25 where R$^7$=R$^2$, it may be necessary to perform an additional step of esterification, by procedures well known to those skilled in the art, after performing the reaction of Equation 19.

Equation 19

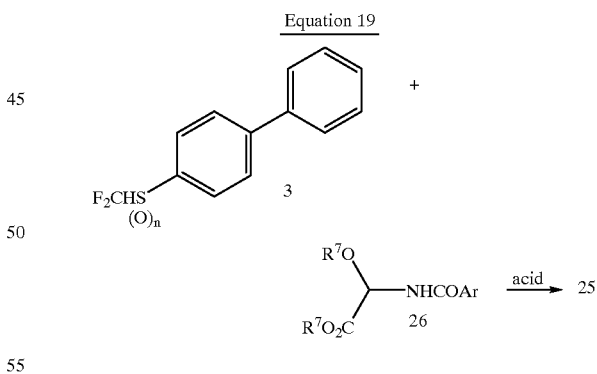

wherein n is 1 or 2;
Ar is as defined for Equation 1;
R$^7$ is H or R$^2$; and
R$^2$ is as defined for Equation 18.

Alternatively, compounds of Formula 24 are prepared by reaction of compounds of Formula 27 with an aroyl halide of Formula 20, according to Equation 20, in analogy with the procedure described for Equation 9.

Equation 20

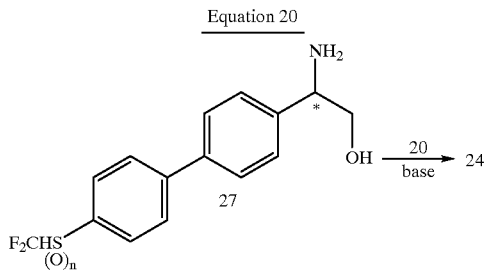

Compounds of Formula 27 are prepared as shown in Equation 21 from compounds of Formula 24 by hydrolysis using procedures well-known to one skilled in the art.

Equation 21

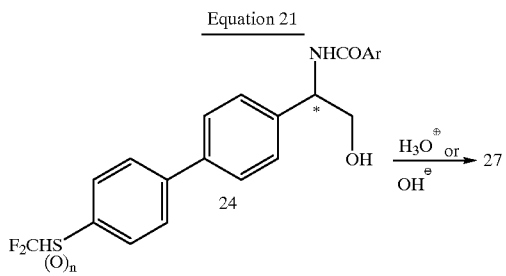

wherein n is 0, 1, or 2; and Ar is phenyl.

Alternatively, compounds of Formula 25 where n is 0 are prepared from compounds of Formula 28 by reaction with excess chlorodifluoromethane in the presence of an alkali-metal hydroxide, alkoxide, or carbonate in a typical solvent such as, but not limited to, tetrahydrofuran, dioxane, ethanol, toluene, or dimethylformamide. Optionally, water can be added as a solvent component; in addition, a catalyst such as a quaternary ammonium salt or a tri(polyoxoalkyl) amine can be used. The reaction is conducted at 0 to 100° C. with the preferred range being 25 to 70° C. The product is isolated by standard procedures well-known to one skilled in the art. Equation 22 illustrates this transformation.

Equation 22

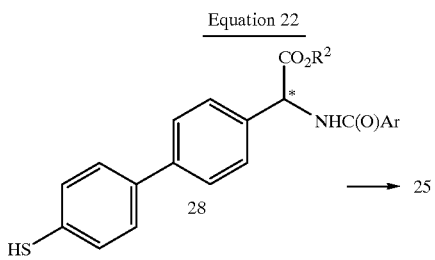

Compounds of Formula 28 are prepared by reduction of compounds of Formula 29 using a metal such as tin or zinc, or tin(II) chloride in conjunction with a mineral acid such as sulfuric acid or hydrochloric acid.

The reaction is conducted in a suitable solvent such as acetic acid, acetone, ethanol or water, at a temperature between 0 to 100° C. typically at 25 to 50° C. The transformation may also be achieved using a member of other reagents well known to one skilled in the art (e.g., EP 687,671-A1). Equation 23 illustrates this transformation.

Equation 23

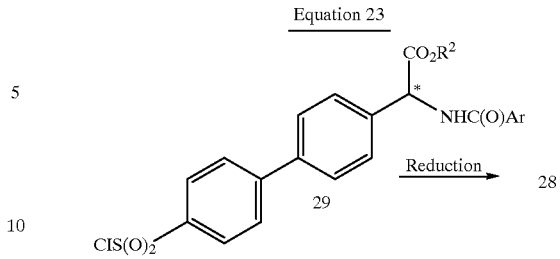

Compounds of Formula 29 can be prepared from compounds of Formula 30 using a reagent prepared from phosphoryl chloride or thionyl chloride and dimethylformamide (*Fieser & Fieser Reagents for Organic Synthesis,* Vol. 1, 284). The reaction is performed in an organic solvent such as N,N-dimethylformamide or dichloroethane, and at a temperature of 0 to 80° C. typically at 25° C. Equation 24 illustrates this transformation.

Equation 24

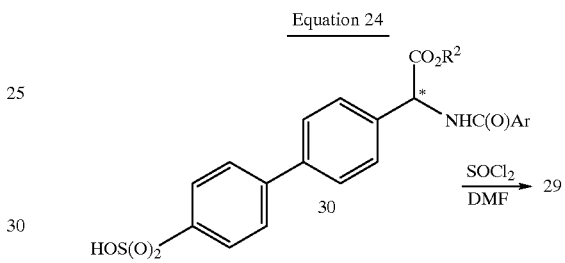

wherein $R^2$ and Ar are as defined for Equation 19.

Compounds of Formula 30 are prepared from compounds of Formula 31 by the use of excess alcoholic solvent such as methanol, ethanol, and the like. An optional anhydrous acid catalyst such as, but not limited to, hydrogen chloride can also be used. The reaction is carried out at −10 to 100° C. but usually at 25° C. Equation 25 illustrates this transformation.

Equation 25

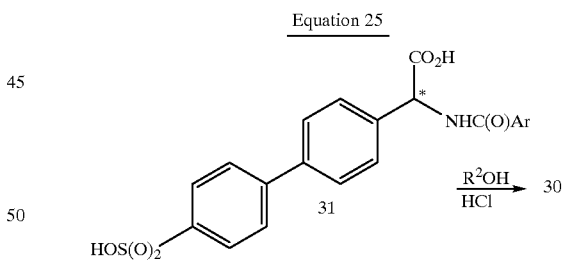

wherein

Ar is as defined for Equation 19.

Compounds of Formula 31 are readily prepared from 4-biphenylsulfonic acid (*Org. React.,* III, 141) and aryl substituted derivatives of 2-hydroxyhippuric acid (*Tetrahedron* 1977, 33, 881), although the procedure for the preparation of the latter is much improved if water is azeotropically removed from the glyoxylic acid by the use of a suitable solvent such as 1,2-dichloroethane or toluene. Ester derivatives and ether derivatives of α-hydroxyhippuric acid are prepared by standard chemical procedures well known to one skilled in the art. The reaction is catalyzed by an acid or Lewis acid such as, but not limited to, sulfuric acid, phosphoric acid or aluminum trichloride. If necessary a suitable organic solvent such as acetic acid, dichloroethane or dichloromethane is used. The temperature of the reaction is in the range −10 to 100° C. with the range 0 to 25° C. being preferred. Equation 26 illustrates this transformation.

Equation 26

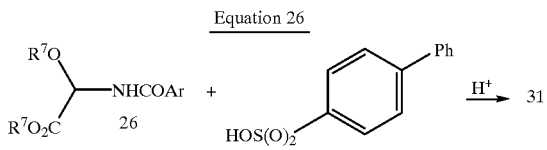

wherein $R^7$ and Ar are as defined for Equation 19.

The methods of Schemes C1–C3 may be accomplished in strict analogy to those of Schemes A1 to A3 (Equations 1 to 13). Compounds of Formula 33 are also prepared by the reaction of an aroyl halide of Formula 20 with amines of Formula 32 in an organic solvent such as ethyl acetate or toluene. Usually an acid scavenger such as triethylamine or aqueous sodium bicarbonate is used. The reaction is performed between −10 to 100° C. with a temperature of 25° C. being preferred. Equation 27 illustrates this transformation.

Equation 27

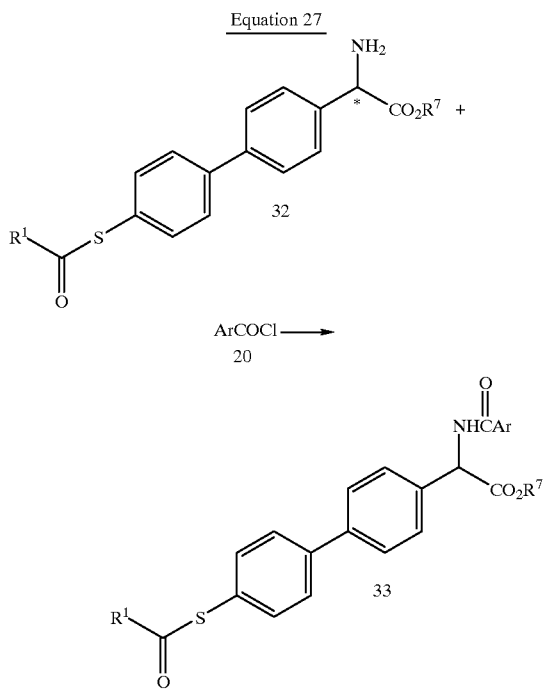

wherein $R^1$ is $N(CH_3)_2$ or $OR^2$;

$R^7$ is H or $R^2$;

$R^2$ is $C_1$–$C_4$ alkyl;

and Ar is as defined for Equation 1.

Carboxylic esters of Formula 32 ($R^7$ is lower alkyl) are prepared from carboxylic acids of Formula 32 ($R^7$ is H) by standard esterification procedures well-known to one skilled in the art.

Biphenylyl glycine derivatives of Formula 32 are readily accessible from compounds of Formula 7 by well-known procedures, such as formylation synthesis, followed by the Strecker amino-acid synthesis (see, for example, J. March, *Advanced Organic Chemistry, Reactions, Mechanisms, and Structure*, 4th edition, J. Wiley & Sons, New York, pp. 545 and 965). Biphenylyl glycine derivatives of Formula 33 are also readily accessible from compounds of Formula 7 by methods analogous to Equation 19.

Salts of Formula 35 (e.g., M is Na) are useful in the preparation of the sulfone of Formula 3 (n is 2) as shown in Equation 28. The known biphenyl sulfonyl chloride, 34, is reduced by standard techniques (Houben-Weyl, *Methoden der Organischen Chemie* 1955, 9, 300), and the resulting sulfinic acid salts are converted to 3 (n is 2) by anyone of a number of methods (e.g., *J. Org. Chem.* 1989, 54, 3023).

Equation 28

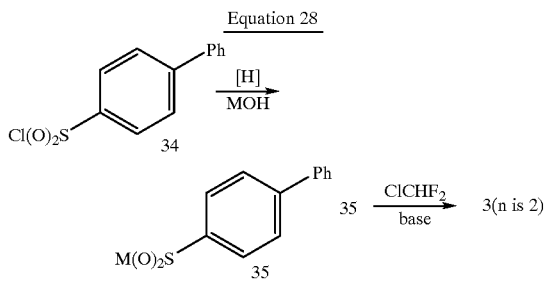

wherein

M is Na, K or Li.

Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; s=singlet, d=doublet, t=triplet, q=quartet, m=multiplet, dd=doublet of doublets, dt=doublet of triplets, br s=broad singlet.

EXAMPLE 1

4'-(2-methyl-1,3-dioxolan-2-yl)[1,1'-biphenyl]-4-thiol

To a dry, 500-mL, three-necked flask equipped with an overhead stirrer, thermometer, reflux condenser with $N_2$ inlet and scrubber was charged 150 mL of anhydrous N,N-dimethylacetamide (DMAc), 31.9 g (0.100 mol) of anhydrous 2-(4'-bromo[1,1'-biphenyl]-4-yl)-2-methyl-1,3-dioxolane (M. E. Sigman, T. Autrey, and G. B. Schuster, *J. Am. Chem. Soc.* 1988, 110, 4197), and 8.3 g (0.12 mol) of anhydrous sodium thiomethoxide. The mixture was heated at ca. 150° C. with a sweep of nitrogen above the condenser into the scrubber. After 1 h, an additional 8.3 g of NaSMe was added, heating was continued for 1 h, and a third 8.3-g portion was added. After about 2 h more, the mixture was allowed to cool to 40° C. and 300 mL of ice-water was added, followed by 12 mL of glacial acetic acid in 50 mL of water. The solids were filtered, washed with water (5×50 mL), suction-dried, and dried in vacuo to afford 27 g of crude mercaptan, which assayed at 94% (GC area, 94% yield). $^1$H-NMR(CDCl$_3$): δ1.7 (s, 3H), 3.5 (s, 1H), 3.8 (m, 2H), 4.1 (m, 2H), 7.35 (d, 2H), 7.45 (d, 2H), 7.55 (s, 4H).

EXAMPLE 2

2-[4'-[(difluoromethyl)thio][1,1'-biphenyl]-4-yl]-2-methyl-1,3-dioxolane

A slurry of 2.7 g (10 mmol) of 4'-(2-methyl-1,3-dioxolan-2-yl)[1,1'-biphenyl]-4-thiol in 10 mL of dimethylformamide was stirred under a atmosphere of chlorodifluoromethane and 1.0 mL of 50% aqueous NaOH was added. The mixture was stirred for 2 h at ambient temperature, neutralized with 30 mL of pH 4 buffer, and extracted with ether. The ether extracts were washed with 1N NaOH, dried (MgSO$_4$) and concentrated to provide the crude product as an orange oil which crystallized on standing. $^1$H-NMR(CDCl$_3$): δ1.7 (s, 3H), 3.8 (m, 2H), 4.1 (m, 2H), 6.85 (t, 1H, J=60 Hz), 7.55 (d, 2H), and 7.6 (m, 6H).

EXAMPLE 3

2-chloro-1-[4'-[(difluoromethyl)thio][1,1'-biphenyl]-4-yl]ethanone and 2-bromo-1-[4'-[(difluoromethyl)thio][1,1'-biphenyl]-4-yl]ethanone A solution of 8.0 g (25 mmol) of 2-[4'-[(difluoromethyl)thio][1,1'-biphenyl]-4-yl]-2-methyl-1,3-dioxolane and 30 mL of anhydrous 1,2-dichloroethane was cooled to 5° C. and sulfuryl chloride (2.3 mL, 3.8 g, 28 mmol) was added via syringe. The solution was allowed to warm to ambient temperature and concentrated to dryness. Acetone (40 mL), 5 mL of water, and 2 mL of 37% HCl were added, and the mixture was heated at 55° C. for 18 h. The mixture was diluted with 20 mL of water with cooling and seeding to precipitate the product. After filtration, washing with cold 50% aqueous MeOH and drying, the crude solid (7.2 g, 92%) was slurried in 80 mL of hot isopropanol (i-PrOH) allowed to cool with good stirring for 30 min, and filtered to afford 5.6 g of 2-chloro-1-[4'-[(difluoro-methyl)thio][1,1'-biphenyl]-4-yl]ethanone, m.p. 102–104° C. A second crop of 0.9 g was obtained by partial concentration of the filtrate. An analytical standard was prepared by chromatography and/or recrystallization from CH$_2$Cl$_2$/MeOH, m.p. 104 to 105° C. $^1$H-NMR(CDCl$_3$): δ4.75 (s, 2H), 6.88 (t, 1H), 7.65 (ABq, 4H) 7.7 (d, A of ABq, 2H), 8.05 (d, B of ABq, 2H).

The analogous bromomethyl ketone was prepared as above, substituting bromine for the sulfuryl chloride and using HBr instead of HCl in the hydrolysis step to provide 2-bromo-1-[4'-[(difluoromethyl)thio][1,1'-biphenyl]-4-yl]ethanone, m.p. 94–96° C. $^1$H-NMR(CDCl$_3$): δ4.45 (s, 2H), 6.88 (t, 1H, J=60 Hz), 7.65 (ABq, 4H), 7.7 (d, A of ABq, 2H), 8.08 (d, B of ABq, 2H).

EXAMPLE 4

S-[4'-(chloroacetyl)[1,1'-biphenyl]-4-yl] dimethylcarbamothioate

A mixture of 38.0 g (0.148 mol) of S-[1,1'-biphenyl]-4-yl dimethylcarbamothioate, 400 mL of dichloromethane, and 14.2 mL (20.1 g, 0.178 mol) of chloroacetyl chloride was cooled to 5° C. and 43 g (0.32 mol) of anhydrous powdered aluminum chloride was added in portions over 20 min at 5 to 10° C. The cooling bath was removed, the tan slurry was allowed to warm to 20° C. held for 20 min at 20° C. and recooled at 5° C. The mixture was poured onto 300 g of ice with good stirring, and allowed to stir for 20 min at ambient temperature. The organic phase was separated, the aqueous phase extracted with 20 mL of CH$_2$Cl$_2$, and the combined extract concentrated to dryness. The residue was slurried with 60 mL of toluene, 200 mL of hexane was added, and the slurry was filtered. The cake was washed with hexane and suction-dried to afford 46.2 g (94% yield) of product as a pale yellow solid, m.p. 144° C. $^1$H-NMR(CDCl$_3$): δ3.1 (br, 6H), 4.72 (s, 2H), 7.6 (ABq, 4H), 7.7 (d of ABq, 2H), 8.03 (d of ABq, 2H); $^{13}$C-NMR(CDCl$_3$): δ36.9, 45.7, 127.4, 127.6, 129.2. 129.5, 133.3, 136.0, 140.2, 145.8, 166.4, 190.5 ppm.

EXAMPLE 5

4'-[2-(2,6-difluorophenyl)-4,5-dihydro-4-oxazolyl][1,1'-biphenyl]-4-thiol (alternatively named 2-(2,6-difluorophenyl)-4,5-dihydro-4-(4'-mercapto[1,1'-biphenyl]-4-yl)oxazole)

A slurry of 12.0 g of S-[4'-[2-chloro-1-(2,6-difluorobenzoyl)amino]ethyl][1,1'-biphenyl]-4-yl] dimethylcarbamothioate in 60 mL of methanol was degassed with nitrogen and charged with 15.0 mL of 25% NaOMe in methanol. The mixture was heated at 60° C. for ca. 5 h, cooled at ambient temperature, and neutralized with 3 mL of acetic acid. The slurry was diluted with 80 mL of water and filtered. The solids were washed with water, suction-dried, and redissolved in dichloromethane. The solution was dried (MgSO$_4$) and concentrated, and the residue was slurry-washed with isopropanol, filtered, and suction-dried to afford 8.7 g (94%) of crude product, m.p. 133–139° C. $^1$H-NMR(CDCl$_3$): δ4.35 (s, 1H, exch w/D$_2$O), 4.35 (t, 1H), 4.82 (dd, 1H), 5.50 (dd, 1H), 7.0 (t, 2H), 7.35 (d, 2H), 7.43 (ABq, 4H), 7.57 (d, 2H).

EXAMPLE 6

4-[4'-[(difluoromethyl)thio][1,1'-biphenyl]-4-yl]-2-(2,6-difluorophenyl)-4,5-dihydrooxazole A solution of 3.7 g of 4'-[2-(2,6-difluorophenyl)-4,5-dihydro4-oxazolyl][1,1'-biphenyl]-4-thiol (alternatively named 2-(2,6-difluorophenyl)-4,5-dihydro-4-(4'-mercapto[1,1'-biphenyl]-4-yl)oxazole) in 15 mL of DMF was purged with nitrogen, cooled to 0° C. charged with 2 mL of liquid chlorodifluoromethane, and 3 mL of 33% aqueous NaOH. The mixture was stirred for 1 h at 5° C. diluted with 80 mL of water, and extracted with toluene. The organic layer was washed with water, dried (MgSO$_4$), and concentrated to an oil. The product was purified by filtration through silica gel with 20% ethylacetate in hexane and crystallization with aqueous isopropanol to afford 2.0 g of product, m.p. 77–79° C. $^1$H-NMR(CDCl$_3$): δ4.35 (t, 1H), 4,85 (dd, 1H), 5.52 (dd, 1H), 6.85 (t, 1H, J=60 Hz), 7.0 (t, 2H), 7.43 (m, 3H), 7.6 (m, 6H).

EXAMPLE 7

(S)-S-[4'-[2-chloro-1-[(2,6-difluorobenzoyl)amino] ethyl][1,1'-biphenyl]-4-yl] dimethylcarbamothioate A dry, 500-mL, sidearm flask equipped with nitrogen inlet, septum, and magnetic stirrer was flushed with nitrogen, charged with 500 mg (2.35 mmol) of [S-(R*,S*)]-2-amino-1,2-diphenylethanol (alternatively named (1S,2R)-(+)-2-amino-1,2-diphenyl-ethanol) and 15 mL of anhydrous tetrahydrofuran (THF), and 3.5 mL (35 mmol) of 10 M borane-dimethylsulfide complex was added via syringe. The solution was stirred for 16 h at ambient temperature to complete the formation of the oxaborolizidine catalyst, and a solution of 16.5 g (50 mmol) of S-[4'-(chloroacetyl)[1,1'-biphenyl]-4-yl] dimethylcarbamothioate in 200 mL of anhydrous THF was added via syringe pump over 2 h. Methanol (1 mL) was added gradually via syringe, followed by 100 mL of 1N HCl. The THF was removed by rotary evaporation under reduced pressure and the solid was filtered, washed with water and dried in vacuo to afford 16.2 g (98%) of chlorohydrin, m.p. 184–185° C. $^1$H-NMR(CDCl$_3$): δ2.95 (d, 1H, OH), 3.1 (br, 6H), 3.7 (d of ABq, 2H), 4.9 (m, 1H), 7.4 (d of ABq, 2H), 7.55 (ABq, 4H), 7.6 (d of ABq, 2H). The e.e. as measured by HPLC (performed using a Regis (S,S)

Whelk-01 1.25 cm×4.6 mm column using 30% i-PrOH/hexane as eluent) was 93%. Part (250 mg, 50%) of the catalyst was recovered by treatment of the aqueous filtrate with caustic and filtration.

A slurry of 3.35 g of (R)-S-[4'-(2-chloro-1-hydroxyethyl)[1,1'-biphenyl]-4-yl] dimethylcarbamothioate and 6 mL of anhydrous pyridine was stirred at 15° C. Methanesulfonyl chloride (1.2 mL) was added gradually via syringe, and the cooling bath was removed. The mixture was allowed to warm to ambient temperature and held for 30 min. Cold water (5 mL) was added, followed by a cold solution of 5 mL of conc. HCl in 20 mL of water. The solids were filtered, washed with three 10-mL portions of water, and dried in vacuo to provide 3.8 g (92%) of chlorohydrin mesylate, m.p. 123–24° C. $^1$H-NMR(CDCl$_3$): δ2.95 (s, 3H), 3.1 (br, 6H), 3.8 (A of ABX, 1H), 3.92 (B of ABX, 1H), 5.72 (X of ABX, 1H), 7.49 (d of ABq, 2H), 7.56 (s, 4H), 7.62 (d of ABq, 2H).

A mixture of 3.2 g of crude, dry (R)-S-[4'-[2-chloro-1-[(methylsulfonyl)oxy]- ethyl][1,1'-biphenyl]-4-yl] dimethylcarbamothioate, 0.60 g of sodium azide and 7 mL of N-methylpyrrolidinone (NMP) was stirred magnetically under nitrogen at 40° C. for 1 h. Water (35 mL) was added and the mixture was filtered, washed with three 15 mL portions of water, and dried in vacuo to afford 3.2 g (97%) of crude azide. $^1$H-NMR(CDCl$_3$): δ3.1 (br, 6H), 3.7 (d, 2H), 4.79 (t, 1H), 7.4 (d of ABq, 2H), 7.56 (s, 4H), 7.62 (d of ABq, 2H).

To a 100-mL sidearm flask equipped with a thermometer and nitrogen bubbler was charged 2.4 g (6.7 mmol) of (S)-S-[4'-(1-azido-2-chloroethyl)[1,1'-biphenyl]-4-yl] dimethylcarbamothioate, 10 mL of ethanol, and 1.0 mL (1.0 g, 8 mmol) of trimethyl phosphite. The mixture was heated at reflux for 1 h, after which heating was removed and 1.1 mL (1.4. g, 14 mmol) of 37% aqueous HCl was added. Heating was resumed for 18 h at reflux and the resulting slurry was cooled to ambient temperature, diluted with 10 mL of diethyl ether, filtered, and suction-dried to afford 2.3 g of amine hydrochloride as a white solid, m.p. 219–221° C. $^1$H-NMR(DMSO-d$_6$): δ3.0 (two br s, 6H), 3.1 (br, 6H), 4.1 (m 2H), 4.7 (m, 1H), 7.5 (d of ABq, 2H), 7.7 (ABq, 4H). 7.75 (d of ABq, 2H), 9.0 (br s, 2H).

To 1.85 g of (S)-S-[4'-(1-amino-2-chloroethyl)[1,1'-biphenyl]-4-yl] dimethylcarbamothioate and 1.0 g of 2,6-difluorobenzoyl chloride in 11 mL of dichloromethane was added to 5 mL of 10% aqueous Na$_2$CO$_3$ solution, and the mixture was stirred at ambient temperature for 30 min. The organic phase was separated, concentrated, and the crude product was washed with water and hexanes and suction-dried to afford 2.14 g of chloro-amide, m.p. 218–220° C. $^1$H-NMR(CDCl$_3$): δ3.08 (two br s, 6H), 4.0 (dq, 1H), 5.6 (m, 1H), 6.75 (br d, 1H), 7.0 (t, 2H), 7.4 (m, 1H), 7.45 (d, 2H), 7.6 (m,6H).

EXAMPLE 8 methyl α-[(2,6-difluorobenzoyl)amino]-4'-[[(dimethylamino)-carbonyl]thio][1,1'-biphenyl]-4-acetate To 10 mL of concentrated sulfuric acid was added 2.31 g of [(2,6-difluorobenzoyl)amino]hydroxyacetic acid (prepared as for the known α-hydroxyhippuric acid from glyoxylic acid and 2,6-difluorobenzamide) and 2.50 g of S-([1,1'-biphenyl]4-yl) dimethylcarbamothioate, and this mixture was stirred for 2 h and poured over ice. The yellow precipitate was collected and washed with water, dissolved in ethyl acetate, and dried over magnesium sulfate. This solution was concentrated until a white precipitate formed, which was collected and washed with 50% ethyl acetate/hexane and dried to afford 2.07 of solid. To a solution of this solid in 15 mL of methanol was added 0.56 mL of thionyl chloride, and this mixture was stirred and heated at reflux for 3.5 h. After the addition of 16 mL of 1N NaOH to the reaction mixture, volatiles were removed on a rotary evaporator, and the residual mixture was extracted with ethyl acetate, and the extract was dried over magnesium sulfate. Concentration of the solution and addition of hexane produced a white solid, which was collected and dried to afford the named compound, 0.27 g. The remaining material was adsorbed onto silica gel, applied to a column of silica gel, and eluted with 60% ethyl acetate/hexane to afford an additional 1.04 g of the named compound. $^1$H-NMR(CDCl$_3$, 300 MHz): δ3.0–3.2 (br d, 6H), 3.8 (s, 3H), 5.8 (d, 1H), 6.9–7.0 (m, 2H), 7.2 (br d, 1H), 7.4 (m, 1H), 7.5–7.6 (m, 8H).

EXAMPLE 9

S-[4'-[1-[(2,6-difluorobenzoyl)amino]-2-hydroxyethyl][1,1'-biphenyl]-4-yl] dimethylcarbamothioate To a solution of 0.27 g material prepared as in Example 8 in 5 mL of dry tetrahydrofuran was added 3.35 mL of commercial 2.0 M tetrahydrofuran solution of lithium borohydride, and this solution was stirred and heated at reflux for 6 h. At room temperature, 4 mL of 1 N aqueous hydrochloric acid solution was added, dropwise, and the mixture was extracted twice with ethyl acetate. The combined organic extracts were washed with water and aqueous sodium chloride solution, dried over magnesium sulfate, and concentrated to a viscous material, 0.30 g, containing some residual solvent. 1H-NMR(CDCl$_3$, 300 MHz): δ2.9–3.1 (br d, 6H), 3.9 (m, 2H), 5.2 (m, 1H), 6.7–6.8 (m, 1H). 6.9 (m, 2H), 7.3–7.6 (m, 9H), as well as resonances for ethyl acetate. This reaction was also repeated with a solution of 0.75 g of ester in 8 mL of tetrahydrofuran and 1.9 mL of 2.0 M lithium borohydride/tetrahydrofuran, with a proportionately scaled work-up procedure, to afford an additional 0.78 g of viscous product, also containing some residual solvent.

EXAMPLE 10

α-(benzoylamino)-4'-sulfo[1,1'-biphenyl]-4-acetic acid

A total of 50 g (0.256 m) of α-hydroxyhippuric acid was added portionwise to 200 mL of concentrated sulfuric acid at −5 to 0° C. When the addition was complete, the mixture was stirred for 20 min and 60 g (0.256 m) of 4-biphenylsulfonic acid was added portionwise. The mixture was stirred at 0 to 5° C. for 5 h and was poured into a mixture of 600 mL of water, salt (72 g), and 50 mL of ethyl acetate at a rate such that the temperature did not exceed 20° C. The mixture was stirred at 25° C. overnight. The mixture was filtered and the gummy solid was washed with 3×50 mL of sodium chloride solution (prepared by mixing equal portions of saturated sodium chloride and water). The solid was dried in a vacuum oven at 70° C. overnight gave 109 g (103% yield) of the crude product contaminated with a little water and sodium chloride.

An analytical sample was prepared by recrystallization from water, m.p. >250° C. IR(Nujol): 3331, 1744, 1641, 1579, 1525, 1489, 1340, 1237, 1188, 1133, 1047, 1012, 1000, 815 cm$^{-1}$. $^1$H-NMR(DMSO-d$_6$): δ5.64 (d, J=7.25 Hz, 1H), 7.47–7.95 (m, 13H), 9.10 (d, J=7.2 Hz, 1H).

EXAMPLE 11 methyl α-(benzoylamino)-4'-sulfo[1,1'-biphenyl]-4-acetate

To a mixture of 12.46 g (30.31 mmol) of α-(benzoylamino)-4'-sulfo[1,1'-biphenyl]-4-acetic acid in 60 mL of methanol was added 6 g of anhydrous hydrogen chloride. When the addition was complete, the mixture was stirred for 2.5 h. The solvent was removed under reduced pressure.

Crystallization from acetone gave 11.47 g (89% yield) of the product as a white solid, m.p. >250° C. IR(KBr): 3440, 1743, 1641, 1529, 1487, 1219, 1038 cm$^{-1}$. $^1$H-NMR(D$_6$-DMSO): δ3.68 (s, 3H), 5.57 (br s, 2H), 5.72 (d, J=6.9 Hz, 1H), 7.44–7.71 (m, 11H), 7.92–7.95 (m, 2H), 9.24 (d, J=6.9 Hz, 1H).

EXAMPLE 12 methyl α-(benzoylamino)-4'-(chlorosulfonyl)[1,1'-biphenyl]-4-acetate

To a mixture of 20.19 g (47.50 mmol) of methyl α-(benzoylamino)-4'-sulfo[1,1'-biphenyl]-4-acetate and 80 mL of DMF was added 13.57 g (0.11 mol) of thionyl chloride at 10 to 12° C. When the addition was complete, the mixture was stirred for 1.5 h and was poured into 300 mL of ethyl acetate. The organic mixture was washed with 4×150 mL of water, was dried, and evaporated gave 14.54 g (69% yield) of product as a solid.

An analytical sample was prepared by recrystallization from ethyl acetate/hexane, m.p. 157–158° C. (d). IR(Nujol): 1735, 1625, 1589, 1535, 1462, 1379, 1279, 1174, 1083, 1012, 822, 753, 713 cm$^{-1}$. $^1$H-NMR(CDCl$_3$): δ5.85 (d, J=6.57 Hz, 1H), 7.32 (d, J=6.57 Hz, 1H), 7.43–7.64 (m, 2H), 7.75–7.77 (m, 2H), 7.78–7.87 (m, 2H), 8.07–8.12 (m, 2H).

EXAMPLE 13 methyl α-(benzoylamino)-4'-mercapto[1,1'-biphenyl]-4-acetate

Hydrogen chloride has was passed through a mixture of 10.17 g (45.07 mmol) of tin(II) chloride dihydrate in 74 mL of acetic acid until the solid had dissolved. A portion of 4.00 g (9.01 mmol) of methyl α-(benzoylamino)-4'-(chlorosulfonyl)[1,1'-biphenyl]-4-acetate was added and the mixture was stirred for 6 h.

The mixture was poured into 500 mL of hydrochloric acid (1N) and the aqueous mixture was extracted with 2×100 mL of ethyl acetate. The combined organic extracts were washed with 2×100 mL of hydrochloric acid (1N) and 75 mL of water and were dried. Removal of the solvent under reduced pressure and chromatography on silica gel (eluted with ethyl acetate/hexane 1:1) gave the product 0.91 g (26% yield) as a white a solid, m.p. 150–152° C. IR(Nujol): 3307, 1739, 1637, 1602, 1580, 1535, 1483, 1377, 1348, 1293, 1175, 1106, 1090, 1002, 805 cm$^{-1}$. $^1$H-NMR(CDCl$_3$): δ3.49 (s, 1H), 3.79 (s, 3H), 5.81 (d, J=6.94 Hz, 1H), 7.22 (d, J=6.75 Hz, 1H), 7.31–7.56 (m, 11H), 7.82–7.85 (m, 2H).

EXAMPLE 14 methyl α-(benzoylamino)-4'-[(difluoromethyl)thio] [1,1'-biphenyl]-4-acetate

A solution of 7.73 g (21.0 mmol) of methyl α-(benzoylamino)-4'-mercapto[1,1'-biphenyl]-4-acetate in 21 mL of DMF was added dropwise to 4.04 g (42.0 mmol) of sodium tert-butoxide in 21 mL of DMF at 10° C. The mixture turned dark orange and was stirred for 15 min. Chlorodifluoromethane was bubbled into the reaction for min. The reaction warmed to ~18° C. The mixture was stirred for 30 min and was poured into 200 mL of hydrochloric acid (1N). The mixture was extracted with ethyl acetate and the combined extracts were washed with water. Drying and removal of the solvent gave the crude product 8.14 g.

Chromatography on silica gel (eluted with ethyl acetate/hexane 1:1) gave the pure product 1.31 g as a solid; m.p. 119–121.5° C. IR(Nujol): 3325, 1748, 1642, 1528, 1487, 1324, 1278, 1223, 1194, 1178, 1065, 1023, 818, 761, 690 cm$^{-1}$. $^1$H-NMR(CDCl$_3$): δ3.81 (s, 3H), 5.83 (d, J=7H, 1H), 6.86 (t, J=5 7 Hz, 1H), 7.24–7.26 (m, 1H), 7.43–7.66 (m, 11H), 7.83–7.86 (m, 2H).

EXAMPLE 15

N-[1-[4'-[(difluoromethyl)thio][1,1'-biphenyl]-4-yl]-2-hydroxyethyl]benzamide

A solution of 5.51 g (12.9 mmol) of methyl α-(benzoylamino)-4'-[(difluoro-methyl)thio][1,1'-biphenyl]-4-acetate in 20 mL of THF was added dropwise to 0.42 g (19.2 mmol) of lithium borohydride in 5 mL of THF at such a rate that the temperature did not exceed 30° C. When the addition was complete, the mixture was stirred for 4 h at room temperature, and was poured into 150 mL of hydrochloric acid (1N). The mixture was extracted with 3×40 mL of ethyl acetate and the combined extracts were dried and evaporated to give the product as a white solid 5.14 g (~100% yield) m.p. 134–136° C. (d) (after washing with a little hexane/ether). $^1$H-NMR(CDCl$_3$): δ4.03 (d, J=4.6 Hz, 2H), 5.28–5.33 (m, 1H), 6.85 (t, J=56.8 Hz, 1H), 7.00 (d, J=6.9 Hz, 1H), 7.41–7.84 (m, 13H). Another sample was prepared by an essentially identical procedure. IR(Nujol): 3216, 1637, 1579, 1530, 1310, 1073, 1004, 820 cm$^{-1}$; m/e (m+1)400.

EXAMPLE 16

β-amino-4'-[(difluoromethyl)thio][1,1'-biphenyl]-4-ethanol

A mixture of 5.14 g of N-[1-[4'-[(difluoromethyl)thio][1,1'-biphenyl]-4-yl]-2-hydroxyethyl]benzamide, 9.5 mL of sodium hydroxide solution (1.54 g, 38.5 mmol in 9.5 mL water), and 36 mL of ethanol was boiled for ~40 h. The mixture was allowed to cool to room temperature and the solvent was removed under reduced pressure. The residue was dissolved in water, and the aqueous mixture was extracted with 3×70 mL of ethyl acetate. The combined extracts were dried and the solvent was removed under reduced pressure. The white solid obtained was washed with a little ether to give the product 2.69 g (70% yield); m.p. 107.5–110.5° C. IR(Nujol): 3333, 3281, 1597 1313, 1073, 1042, 895, 820 cm$^{-1}$. $^1$H-NMR(CDCl$_3$): δ3.56–3.63 (m, 1H), 3.76–3.81 (m, 1H), 4.09–4.13 (m, 1H), 6.86 (t, J=57.0 Hz, 1H), 7.41–7.65 (m, 8H).

Treatment of the mother liquors with hydrogen chloride afforded a further 0.6 g (14% yield) of the product as the hydrochloride salt.

EXAMPLE 17

N-[1-[4'-[(difluoromethyl)thio] [1,1'-biphenyl]-4-yl]-2-hydroxyethyl]-2,6-difluorobenzamide A solution of 0.137 g (0.776 mmol) of 2,6-difluorobenzoyl chloride in 1 mL of dichloromethane was added dropwise to a mixture of 0.23 g (0.693 mmol) of β-amino- 4'-[(difluoromethyl)thio][1,1'-biphenyl]-4-ethanol hydrochloride salt, 1.5 mL of dichloromethane, and 1.5 mL of sodium bicarbonate (saturated aqueous solution). The mixture was stirred for 2 h, and was diluted with 10 mL of water. The mixture was extracted with 3×20 mL of dichloromethane, 35 mL of dichloromethane and the organic phase separated. The combined extracts were dried and evaporated. Chromatography on silica gel (eluted with ethyl acetate/hexane (1:1)) gave the product 0.28 g (93% yield) as a white solid m.p. 156.5–157° C. IR(Nujol): 3294, 1649, 1624, 1589, 1535, 1309, 1233, 1071, 1004, 819 cm$^{-1}$. $^1$H-NMR(CDCl$_3$): δ2.15 (t, J=5.75 Hz, 1H), 4.03–4.06 (m, 2H), 5.33–5.37 (m, 1H), 6.81 (d, J=7.2 Hz, 1H), 6.86 (t, J=57 Hz, 1H), 6.94–6.99 (m, 2H), 7.35–7.43 (m, 1H), 7.48 (d, J=8 Hz, 2H), 7.50–7.65 (m, 6H).

EXAMPLE 18

N-[2-chloro-1-[4'-[(difluoromethyl)thio][1,1'-biphenyl]-4-yl]ethyl]-2,6-difluorobenzamide A portion of 0.37 g (3.1 mmol) of thionyl chloride was added to 1.20 g (2.75 mmol) of N-[1-[4'-[(difluoromethyl)thio][1,1-biphenyl]4-yl]-2-hydroxyethyl]-2,6-difluorobenzamide and 10 mL of toluene. The mixture was warmed to 45° C. for 3.25 h. An additional portion of 0.25 g (2.1 mmol) of thionyl chloride was added and the mixture was stirred for an additional 1 h. The mixture was cooled to 25° C. and the solvent removed under reduced pressure gave the product 1.18 g (96% yield) as an off-white solid. Chromatography on silica gel (eluted with ethyl acetate/hexanes, 1:2) afforded an analytical sample; m.p. 146–147° C. IR (Nujol): 3290, 1652, 1625, 1539, 1311, 1234, 1065, 1009, 818 cm$^{31\ 1}$. $^1$H-NMR(CDCl$_3$): δ3.96–4.08 (m, 2H), 5.62–5.68 (m, 1H), 6.65 (d, J=7.3 Hz, 1H), 6.86 (t, J=57 Hz, 1H), 6.95–7.02 (m, 2H), 7.30–7.48 (m, 3H), 7.50–7.67 (m, 6H).

EXAMPLE 19

4-[4'-[(difluoromethyl)thio][1,1'-biphenyl]-4-yl]-2-(2,6-difluorophenyl)-4,5-dihydrooxazole A portion of 0.093 g (1.16 mmol) of sodium hydroxide solution (50%) was added dropwise to 0.53 g (1.16 mmol) of N-[2-chloro-1-[4'-[(difluoromethyl)thio][1,1'-biphenyl]-4-yl]ethyl]-2,6-difluorobenzamide in 3.5 mL of DMF. After 3 h, a further portion, 0.045 g (0.56 mmol) of sodium hydroxide solution (50%) was added. When the reaction was completed by TLC, the mixture was poured into water (50 mL). The aqueous mixture was extracted with 3×50 mL of ethyl acetate. The combined extracts were dried and the solvent was removed under reduced pressure. The residue was dissolved in 100 mL of ether. The ethereal solution was washed with 50 mL of water, dried, and the solvent was removed under reduced pressure gave the product, 0.35 g (72% yield), as a pale yellow solid, indistinguishable from the product of Example 6.

EXAMPLE 20

N-(chloroethenyl)-2,6-difluorobenzamide

A mixture of 5 g (31.8 mmol) of 2,6-difluorobenzamide, 6 g (31 mmol) p-toluenesulfonic acid monohydrate, and 35 mL of 1,2-dichloroethane was boiled.

The water azeotrope was removed and additional 1,2-dichloroethane was added as necessary. A portion of 10 g (63.6 mmol) of chloroacetaldehyde (50%) was added as rapidly as possible to the mixture. The water azeotrope was removed, and 1,2-dichloroethane added as required. When the head temperature had reached ~80° C. a further portion of 5 g (31.8 mmol) of chloroacetaldehyde (50%) was added to the mixture. The distillation was continued until the head temperature had reached ~83° C. The mixture was allowed to cool to room temperature and was poured into 100 mL of sodium bicarbonate (sat). The mixture was diluted with 80 mL of 1,2-dichloroethane and was filtered. The organic phase was separated. The solid from the filtration was dissolved in 100 mL of ethyl acetate and combined with the organic phase. The combined organic extracts were dried and the solvent was removed under reduced pressure to give a gummy solid; 5.8 g.

A small portion 0.5 g of the product was purified by chromatography on silica gel (eluted with ethyl acetate/hexane 2:3) gave the pure product 0.18 g, m.p. 69.5–72° C. IR(Nujol): 3351, 3231, 3084, 1658, 1626, 1593, 1494, 1318, 1282, 1232, 1144, 1082, 1055, 1010, 996, 969, 901, 884 cm$^{-1}$. $^1$H-NMR(CDCl$_3$): δ5.63 (d, J=6 Hz, 1H), 6.99–7.04 (m, 2H), 7.35–7.39 (m, 1H), 7.42–7.49 (m, 1H), 7.96 (br s, 1H). HRMS calculated for C$_9$H$_6$ ClF$_2$NO is 217.0106, found 217.0116.

EXAMPLE 21

S-[4'-[2-chloro-1-[(2,6-difluorobenzoyl)amino]ethyl]-[1,1'-biphenyl]-4-yl] dimethylcarbamothioate A solution of 1 g (4.59 mmol) N-(chloroethenyl)-2,6-difluorobenzamide in 2 mL of dichloromethane was added to 4 mL of concentrated sulfuric acid at 0° C. A portion of 1 g (3.89 mmol) of S-[1,1'-biphenyl]-4-yl dimethylcarbamothioate was added to the mixture and the mixture was stirred at 0° C. for 2 h. The mixture was stored in the refrigerator overnight. The mixture was poured into water (100 mL) and the mixture was filtered. The solid was washed with water (100 mL) and was dried overnight in vacuo at 70° C. to give the crude product 1.52 g (84% yield) as solid.

A small portion 0.5 g was further purified by chromatography on silica gel (eluted with dichloromethane/ethyl acetate 9:1) to give the product as a solid (0.18 g). IR(Nujol): 3310, 1665, 1625, 1590, 1562, 1529, 1302, 1261, 1232, 1091, 1051, 1004, 909, 817 cm$^{-1}$. $^1$H-NMR(CDCl$_3$): δ3.08 (two br s, 6H), 4.0 (dq, 1H), 5.6 (m, 1H), 6.75 (br d, 1H), 7.0 (t, 2H), 7.4 (m, 1H), 7.45 (d, 2H), 7.6 (m, 6H).

EXAMPLE 22

α-(chloromethyl)-4'-[(difluoromethyl)thio][1,1'-biphenyl]-4-methanol

A mixture of 3.0 g of 2-chloro-1-[4'-[(difluoromethyl)thio][1,1'-biphenyl]-4-yl]ethanone, 15 mL of THF, and 2 mL of pH 7 buffer was cooled to 5–10° C. 160 mg of NaBH$_4$ was added, and stirring was continued for 1 h. The mixture was concentrated and triturated with water, filtered, and the solids were washed with hexane and dried in vacuo to afford 2.4 g (80%) of product, m.p. 66–68° C. $^1$H-NMR(CDCl$_3$): δ2.82 (d, 1H, OH), 3.7 (ddd, 2H), 4.95 (m, 1H), 6.85 (t, 1H, J=60 Hz), 7.5 (d of AB q, 2H), 7.6 (m, 6H).

EXAMPLE 23

N-[2-chloro-1-[4'-[(difluoromethyl)thio][1,1'-biphenyl]-4-yl]ethyl]-2,6-difluorobenzamide A mixture of 2.0 g of α-(chloromethyl)-4'-[(difluoromethyl)thio][1,1'-biphenyl]-4-methanol, 4.0 g of 2,6-difluorobenzonitrile, and 15 mL of dichloromethane was cooled to 5° C. and 0.8 mL of conc. sulfuric acid was added dropwise over 7 min. After 30 min, ice was added, the mixture was diluted with hexanes, and the crude product was filtered and dried to afford 1.0 g of product, m.p. 144–145° C. $^1$H-NMR (CDCl$_3$): δ4.0 (dq, 2), 5.6 (m, 1H), 6.75 (br d, 1H), 6.85 (t, 1H, J=60 Hz), 7.0 (t, 2H), 7.4 (m, 1H), 7.5 (d, 2H), 7.6 (m, 6H). The filtrate was extracted with ethyl acetate; the extract was washed with water, concentrated, and chromatographed on silica gel to afford an additional 0.5 g of product, corresponding to a total yield of 52%.

EXAMPLE 24

(S)-S-[4'-[2-(2,6-difluorophenyl)-4,5-dihydro-4-oxazolyl]-[1,1'-biphenyl]-4-yl] dimethylcarbamothioate A sample of (S)-S-[4'-[2-chloro-1-[(2,6-difluorobenzoyl)amino]ethyl][1,1'-biphenyl]-4-yl] dimethylcarbamothioate prepared from 2.3 g of (S)-S-[4'-(1-amino-2-chloroethyl)[1,1'-biphenyl]-4-yl] dimethylcarbamothioate and 1.5 g of 2,6-difluorobenzoyl chloride as above was purified by washing with EtOAc/hexanes, then with i-PrOH and suction-dried. This was slurried in 50 mL of toluene, 50 mg of tetrabutylammonium bromide and 1.0 g of 50% aqueous NaOH were added, and the mixture was stirred rapidly for 1 h, the toluene layer was decanted, washed with water, dried (MgSO$_4$), and concentrated. The residue was triturated with i-PrOH to afford 1.7 g of product, m.p. 135–136° C. $^1$H-NMR (CDCl$_3$): δ3.1 (br, 6H), 4.35 (t, 1H), 4.85 (dd, 1H), 5.52 (dd, 1H), 7.0 (t, 2H), 7.4 (m, 3H), 7.6 (m, 6H).

EXAMPLE 25

(S)-4'-[2-(2,6-difluorophenyl)-4,5-dihydro-4-oxazolyl][1,1'-biphenyl]-4-thiol

A mixture of 0.60 g of (S)-S-[4'-[2-(2,6-difluorophenyl)-4,5-dihydro-4-oxazolyl][1,1'-biphenyl]-4-yl] dimethylcarbamothioate, 5 mL of methanol, and 0.30 g of 25% NaOMe solution was heated at 60° C. for 7 h and allowed to stand at ambient temperature for 3 d. After adding 0.5 mL of acetic acid and 5 mL of water, the product was filtered, washed with water, and suction-dried to afford 0.30 g of product, m.p. 133–135° C. The $^1$H NMR (CDCl$_3$) spectrum was the same as that of the racemic product of Example 5.

EXAMPLE 26

(+/−)-4-(1-azido-2-chloroethyl)-4'-[(difluoromethyl)thio][1,1'-biphenyl]

A solution of 5.3 g of α-(chloromethyl)-4'-[(difluoromethyl)thio][1,1'-biphenyl]-4-methanol and 10 mL of anhydrous pyridine was stirred at 10° C. Methanesulfonyl chloride (2.0 mL) was added gradually via syringe, and the cooling bath was removed. The mixture was allowed to warm to ambient temperature and held for 30 min. Cold water (5 mL) was added, followed by a 80 mL of 2N HCl. The mixture was extracted with ethyl acetate, washed with water, dried, and concentrated to afford the crude mesylate. This was stirred with 1.0 g of sodium azide, 5 mL of water, 0.22 g of tetrabutylammonium bromide and 20 mL of toluene at 50° C. for 6 h, cooled and separated. The toluene phase was washed with water, concentrated, and chromatographed on silica gel to provide 4.0 g (70% overall) of product as an oil. $^1$H-NMR(CDCl$_3$): 3.7 (d, 2H), 4.8 (t, 1H), 6.85 (t, 1H, J=60 Hz), 7.4 (d of AB q, 2H), 7.6 (m, 6H).

EXAMPLE 27

(+/−)-α-(chloromethyl)-4'-[(difluoromethyl)thio][1,1'-biphenyl]-4-methanamine hydrochloride A solution of 4.0 g of (+/−)-4-(1-azido-2-chloroethyl)-4'-[(difluoromethyl)thio]-[1,1'-biphenyl], 15 mL of toluene, and 2.0 g of trimethyl phosphite was heated at 50° C. for 1 h, and 50 mL of hexanes and 1 mL of 1N HCl was added. The mixture was allowed to stir at ambient temperature for 1 h, whereupon the product crystallized. Filtration and washing with hexanes afforded 2.0 g of product, m.p. 131–133° C. $^1$H-NMR(CDCl$_3$) δ3.6 (d, 3H), 3.75 (d, 3H), 3.8 (m, 2H), 4.6 (m, 1H), 6.85 (t, 1H, J=60 Hz), 7.45 (d of AB q, 2H), 7.6 (m, 7H). A portion of this material (1.8 g) was heated at reflux with 10 mL of methanol and 0.53 g of conc. HCl for 24 h, cooled, diluted with ether, and filtered to afford 1.3 g of product, m.p. 168–171° C. (d). $^1$H-NMR (DMSO-d$_6$): δ4.1 (m, 2H), 4.7 (t, 1H), 7.5 (t, 1H, J=60 Hz), 7.6 to 7.8 (m, 8H), 9.0 (br s, 3H).

EXAMPLE 28

(+/−)-N-[2-chloro-1-[4'-[(difluoromethyl)thio][1,1'-biphenyl]-4-yl]ethyl]-2,6-difluorobenzamide To a slurry of 1.1 g of (+/−)-α-(chloromethyl)-4'-[(difluoromethyl)thio][1,1'-biphenyl]-4-methanamine hydrochloride in 13 mL of ethyl acetate was added 0.60 g of 2.6-difluorobenzoyl chloride. 0.60 g of sodium bicarbonate, and 3 mL of water. After 15 min, ethyl acetate was added and the organic phase was washed with aqueous NaCl, dried (MgSO$_4$), filtered, and concentrated to dryness. The residue was triturated with toluene/hexanes, filtered, washed with hexanes, and suction-dried to afford 1.22 g of product, m.p. 148–150° C. $^1$H-NMR (CDCl$_3$): δ4.0 (dq, 2H), 5.6 (m, 1H), 6.75 (br d, 1H), 6.85 (t, 1H, J=60 Hz), 7.0 (t, 2H), 7.4 (m, 1H), 7.5 (d, 2H), 7.6 (m, 6H).

EXAMPLE 29

4-[4'-[(difluoromethyl)thio][1,1'-biphenyl]-4-yl]-2-(2,6-difluorophenyl)-4,5-dihydrooxazole To a well-stirred mixture of 0.6 g of 25% aqueous NaOH, 70 mg of tetrabutylammonium bromide (TBAB) and 10 mL of toluene was added 1.0 g of (+/−)-N-[2-chloro -1-[4'-[(difluoromethyl)thio][1,1'-biphenyl]-4-yl]ethyl]-2,6-difluorobenzamide as a solid. After 45 min, 2 mL of water was added along with 10 mL of diethyl ether. The organic phase was washed with water, dried (MgSO$_4$), filtered, and concentrated to dryness. The residue was triturated with hexanes, filtered, and suction-dried to afford 0.70 g of product, m.p. 75–77° C. The $^1$H-NMR (CDCl$_3$) spectrum was the same as that the product of Example 6.

EXAMPLE 30

4-[4'-[(difluoromethyl)sulfonyl][1,1'-biphenyl]-4-yl]-2-(2,6-difluorophenyl)4,5-dihydrooxazole A 1.67 g sample of 4-[4'-[(difluoromethyl)thio][yl,yl'-biphenyl]-4-yl]-2-(2,6-difluorophenyl)-4,5-dihydrooxazole was dissolved in 30 mL of ethyl acetate, 12.8 g of dibasic sodium phosphate was added and this suspension was stirred at ambient temperature while commercial 32% peracetic acid solution in acetic acid was added dropwise. After the reaction mixture had stirred overnight, it was treated with 20 mL of water and 20 mL of saturated aqueous sodium bisulfite, and this mixture was stirred for 30 min. The organic layer was separated, and was washed with saturated aqueous sodium carbonate solution, water, and brine, dried over magnesium sulfate, and concentrated under vacuum. The residue was recrystallized from ether/hexanes and the resultant solid collected on a glass frit, washed with 2:1 ether/hexanes and vacuum-dried to obtain the title compound as a white solid, 1.17 g of product, m.p. 115–117° C. $^1$H NMR (CDCl$_3$): δ4.3–4.4 (m, 1H), 4.8–4.9 (m, 1H), 5.5–5.6 (m, 1H), 6.22 (t, 1H), 7.0 (m, 2H), 7.4–7.5 (m, 3H), 7.6–7.7 (m, 2H), 7.8–7.9 (m, 2H), 8.0–8.1 (m, 2H).

EXAMPLE 31

[1,1'-biphenyl]-4-thiol (alternatively named 4'-mercapto-1,1'-biphenyl)

A mixture of 228 g of S-[ 1,1 '-biphenyl]-4-yl dimethylcarbamothioate, 500 mL of methanol, and 250 g of aqueous 50% NaOH was heated at reflux for 40 minutes, cooled to 50° C. and 320 g of concentrated HCl was carefully added along with about 2 L of ice. The mixture was filtered, washed with water, and suction-dried overnight to afford 160 g (97% yield) of product, m.p. 108–110° C.

EXAMPLE 32

S-([1,1'-biphenyl]-4-yl) O-(2-methylpropyl) carbonothioate

A mixture of 9.3 g of [1,1'-biphenyl]-4-thiol (alternatively named 4'-mercapto-1,1'-biphenyl), 40 mL of dichloromethane, 0.21 g of tetrabutylammonium hydrogen sulfate, and 7.2 g of isobutyl chloroformate was cooled to 5° C. and 10.2 g of 20% aqueous NaOH was added over 10 min. The mixture was allowed to stir for 30 min at 15° C. the phases were separated, and the organic phase was concentrated to dryness. The residue was slurried in 100 mL of cold isopropanol, filtered, and suction-dried to afford 12.9 g (92% yield) of product, m.p. 78–79° C. $^1$H NMR (CDCl$_3$): δ0.90 (d, 6H), 2.00 (s, 1H), 4.05 (d, 7.35–7.50 (m, 3H), 7.60 (d, 2H), 7.60 (s, 4H).

EXAMPLE 33

S-[4'-(chloroacetyl)[yl, 1,1'-biphenyl]-4-yl] O-(2-methylpropyl) carbonothioate

A mixture of 12.5 g of anhydrous AlCl$_3$ and 50 mL of dichloromethane was cooled to –5° C. and a solution of 5.05 g of chloroacetyl chloride and 12.7 g of S-([1,1'-biphenyl]-4-yl) O-(2-methylpropyl) carbonothioate in 30 mL of dichloromethane was added over 10 min, and the mixture was allowed to stir for 1 h at 10–15° C. The mixture was poured carefully onto ice-water and allowed to stir overnight at ambient temperature. The phases were separated, the organic layer was concentrated to dryness, and the residue was stirred with 100 mL of isopropanol, filtered, washed with isopropanol, and suction-dried to afford 14.7 g (92% yield) of product, m.p. 108–110° C. $^1$H NMR (CDCl$_3$): δ0.90 (d, 6H), 2.00 (s, 1H), 4.05 (d, 2H), 4.73 (s, 2H), 7.65 (s, 4H), 7.71 (d, 2H), 8.05 (d, 2H).

EXAMPLE 34

(+/–)-S-[4'-[2-chloro-1-[(2,6-difluorobenzoyl)amino] ethyl]-[1,1'-biphenyl]-4-yl] O-(2-methylpropyl) carbonothioate A mixture of 11.3 g of S-[4'-(chloroacetyl)[1,1'-biphenyl]-4-yl] O-(2-methyl-propyl) carbonothioate, 160 mg of acetic acid, 3 mL of water, and 50 mL of THF was cooled to 10° C. and 500 mg of sodium borohydride was added in portions over 15 min. The mixture was allowed to stir at ambient temperature for 10 min, 20 mL of water was added, and the mixture was concentrated to remove most of the THF. The aqueous slurry was extracted with ethyl acetate, the organic phase was washed with water and concentrated to dryness. The residue was washed with hexanes and suction-dried to afford 10.1 g (89%) of chlorohydrin, m.p. 94–95° C. $^1$H NMR (CDCl$_3$): δ0.95 (d, 6H), 2.00 (s, 1H), 2.72 (d, 1H), 3.70 (dd, 1H), 3.79 (dd, 1H), 4.04 (d, 2H), 495 (dt, 1H), 7.47 (d, 2H), 7.60 (d, 2H), 7.60 (s, 4H).

A solution of 20.0 g of 2.6-difluorobenzonitrile in 20 mL of dichloromethane was cooled to 5° C. and 13 g of conc H$_2$SO$_4$ was added. The mixture was stirred vigorously while adding 15.0 g of (+/–)-S-[4'-(2-chloro-1-hydroxyethyl)[1,1'-biphenyl]-4-yl] O-(2-methylpropyl) carbonothioate over 5 min at 5–10° C. After 30 min, the mixture was poured onto ice with stirring and 100 mL of water and 100 mL of hexanes was added. A solution of 15 mL of aqueous 26% NH$_4$OH in 100 mL of water was added and the mixture was stirred for 1 h at ambient temperature to crystallize the product. Filtration, washing with water and hexanes, and suction-drying afforded 19.4 g (94%) of product, m.p. 171–173° C. $^1$H NMR (CDCl$_3$): δ0.90 (s, 6H), 2.00 (s, 1H), 4.02 (m, 2H), 4.05 (d, 2H), 5.65 (dt, 1H), 6.65 (br d, 1H), 7.0 (t, 2H), 7.40 (m, 1H), 7.49 (d, 2H), 7.60 (s, 4H), 7.62 (d, 2H).

EXAMPLE 35

4'-[2-(2,6-difluorophenyl)-4,5-dihydro-4-oxazolyl] [1,1'-biphenyl]-4-thiol (alternatively named 2-(2,6-difluorophenyl)-4,5-dihydro-4-(4'-mercapto,[1,1'-biphenyl]-4-yl)oxazole)

A mixture of 2.10 g of (+/–)-S-[4'-[2-chloro-1-[(2,6-difluorobenzoyl)amino]-ethyl][1,1'-biphenyl]-4-yl] O-(2-methylpropyl) carbonothioate, 1.5 g of aqueous 50% NaOH, and 30 mL of methanol was heated under nitrogen at reflux for 5 min, cooled, diluted with water, and acidified with acetic acid. The precipitated product was filtered, washed with water, and suction-dried to afford 1.46 g (95% yield) of product, NMR same as in Example 5.

EXAMPLE 36

N,N'-[oxybis(2-chloroethylidene)]bis[2,6-difluorobenzamide]

A mixture of 50 g (0.318 mol) 2,6-difluorobenzamide, 70 g (0.445 mol) of aqueous chloroacetaldehyde (50% w/w), 0.6 g (3.15 mol)p-toluenesulfonic acid monohydrate, and 81 mL of dichloromethane was boiled. The dichloromethane/water azeotrope was removed via a ten plate Oldershaw column, and the water was separated in a decanting condenser. Dichloromethane was returned from the decanting condenser to the top of the Oldershaw column and then to the reaction flask. The mixture was boiled for a total of 23 h, and was stirred at room temperature for a total of 48 h.

The mixture was filtered to give the product as a white solid 64.80 g, 89% m.p. 171–171.5° C. (dec) (after recrystallization from ethyl acetate). IR (Nujol): 3197, 1658, 1622, 1552, 1358, 1307, 1236, 1190, 1034, 1009, 794 cm$^{-1}$. $^1$H-NMR(D$_6$-DMSO): 3.75–3.62 (m, 4H), 5.74–5.66 (m, 2H), 7.25–7.17 (m, 4H), 7.62–7.51 (m, 2H), 9.54 (d, J=8.45 Hz, 2H). HRMS calculated for C$_{18}$H$_{15}$Cl$_2$F$_4$N$_2$O$_3$ (M+H$^+$) is 453.0396, found 453.0384.

EXAMPLE 37

N-[2-chloro-1-[4'-[(difluoromethyl)sulfonyl]-[1,1'-biphenyl]-4-yl]ethyl]-2,6-difluorobenzamide To 40 mL of sulphuric acid at 5° C. was added 6.04 g (22.5 mmol) of 4-[(difluoromethyl)sulfonyl]-1,1'-biphenyl.

A slurry of 5.10 g (11.3 mmol) of N,N'-[oxybis(2-chloroethylidene)]bis[2,6-difluorobenzamide] in 10 mL of dichloromethane was added so that the temperature did not exceed 10° C. The mixture was allowed to warm to 15° C. and was stirred for 375 min. The mixture was added dropwise to a mixture of 240 mL of water and 108 mL of dichloromethane. The mixture was stirred for 30 min. The organic layer was removed and was washed with 100 mL of sodium hydroxide solution (0.1N), 100 mL of water, was dried, and evaporated under reduced pressure. Crystallization from 40 mL of isopropanol afforded 7.65 g (69%) of the product as a white solid. M.p. 146–149° C.

IR(Nujol): 3298, 1659, 1627, 1594, 1530, 1349, 1303, 1233, 1202, 1188, 1162, 1104, 1080, 1006, 902, 818 cm$^{-1}$. $^1$H-NMR(CDCl$_3$): δ3.96–4.08(m, 2H), 5.63–5.69(m, 1H), 6.22 (t, J=53.4 Hz, 1H), 6.72(d, J=7.7 Hz, 1H), 6.99(t, J=8.2 Hz, 2H), 7.37–7.46(m, 1H), 7.54(d, J=8.4 Hz, 2H), 7.66(d, J=8.2 Hz, 2H), 7.82(d, =8.2 Hz, 2H), 8.04(d, J=8.2 Hz, 2H).

EXAMPLE 38

4-[(difluoromethyl)thio]-1,1'-biphenyl

To a 500-mL three-necked flask equipped with thermometer, nitrogen bubbler, gas inlet tube, overhead stirrer, vented addition funnel, gas-addition funnel, and cold-finger condenser was charged 45.0 g (0.242 mol) of [1,1'-biphenyl]-4-thiol and 150 mL of N,N-dimethylacetamide (DMAc). The system was degassed by a subsurface nitrogen purge, cooled to 0–5° C. and charged with 30 mL of liquefied chlorodifluoromethane. A solution of aqueous 50% NaOH (30 mL, 45 g, 0.56 mol) was added over about 20 min, allowing the mixture to exotherm to 28° C. over the course of the addition. The mixture was held at 25–30° C. for an additional 30 minutes, carefully diluted with 250 mL of water, and the precipitated product was filtered, washed with three 100-mL portions of water, thoroughly slurry-washed with 200 mL of water, and dried for 18 h at 50° C./100 mm to afford 56.0 g (98% yield) of product as a pale brown solid. A sample was purified by recrystallization from isopropanol, m.p. 56–57° C. IR(KBr): 1479, 1323, 1311, 1060, 1037, 1022, 770, 763, 748, 700 cm$^{-1}$. $^1$H-NMR(CDCl$_3$): δ6.86 (t, 1H, J=60 Hz), 7.35–7.5 (m, 3H), 7.6 (m, 6H). $^{13}$C-NMR (CDCl$_3$): δ120.9 (t, J$_{CF}$=275 Hz), 124.8 (t, J$_{CF}$=2 Hz), 127.1, 127.9, 128.0, 128.9. 135.7, 139.8, 142.8 ppm. $^{19}$F-NMR (CDCl$_3$) δ–90.7 (d, J$_{HF}$=57 Hz).

EXAMPLE 39

4-[(difluoromethyl)sulfonyl]-1,1'-biphenyl

To a 1-L three-necked flask equipped with an overhead stirrer, thermometer, and vented addition funnel was charged 71.8 g (0.304 mol) of 4-[(difluoromethyl)thio]-1,1'-biphenyl, 280 mL of glacial acetic acid, and 3.0 g of sodium tungstate predissolved in 10 mL of water. The mixture was heated to 60° C., heating was removed, and 90 mL (0.87 mol, 2.9 equiv) of 30% hydrogen peroxide was added dropwise, maintaining the temperature at 60–70° C. After the addition was complete, the mixture was heated at 80° C. for 2 h to finish the conversion. The solution was cooled to 25° C. and 140 mL of water was added gradually to complete precipitation of the product. The product was filtered, washed with three 50-mL portions of water, suction-dried, then washed with 150 mL of isopropanol, suction-dried, and oven-dried at 50° C./150 mm to afford 78 g (96%) of ca. 98%-pure 4-[(difluoromethyl)sulfonyl]-1,1'-biphenyl, m.p. 81–83° C. An analytical sample prepared by recrystallization from isopropanol/water had m.p. 83–85° C. IR(KBr): 1593, 1334, 1159, 1113, 1080, 754, 607 cm$^{-1}$. $^1$H-NMR(CDCl$_3$): δ6.22 (t, 1H, J=60 Hz), 7.5 (m, 3H), 7.62 (dd, 2H, 7.82 (d, 2H), 8.05 (d, 2H). $^{13}$C-NMR (CDCl$_3$): δ114.7 (t, J$_{CF}$=286 Hz), 127.4, 128.1, 129.1, 129.2, 130.1, 131.1, 138.6, 148.8 ppm. $^{19}$F-NMR (CDCl$_3$): δ–120.5 (d, J$_{HF}$=53.4 Hz).

EXAMPLE 40

2-chloro-1-[4'-[(difluoromethyl)sulfonyl][1,1'-biphenyl]-4-yl]ethanone

To a 500-mL sidearm flask equipped with a vented addition funnel, overhead stirrer, thermometer, and nitrogen bubbler connected to a caustic scrubber was charged 26.8 g (0.098 mol, assay=98%) 4-[(difluoromethyl)sulfonyl]-1,1'-biphenyl, of 13.4 g (0.20 mol) of chloroacetyl chloride, and 150 mL of dichloromethane. Granular anhydrous aluminum chloride (28.0 g, 0.210 mol) was added in portions over 20 minutes, and the mixture was allowed to stir at 25–30° C. for 8–18 h. The violet solution was poured onto 300 g of ice with efficient stirring, 300 mL of dichloromethane was added to the resulting yellow slurry, and the mixture was filtered to remove undissolved 4'-(chloroacetyl)[1,1'-biphenyl]-4-sulfinic acid. After phase separation, the dichloromethane solution was washed with aqueous HCl, aqueous NaHCO$_3$, dried with MgSO$_4$, filtered, and concentrated to dryness. The residue was slurried in 200 mL of isopropanol, filtered, and washed with 50 mL of isopropanol to afford 27.7 g (ca. 79%) of crude 2-chloro-1-[4'-[(difluoromethyl)sulfonyl][1,1'-biphenyl]-4-yl]ethanone as a pale yellow solid assaying at 96% by gc-area. A 98%-pure sample was obtained by chromatography on silica-gel and crystallization from EtOAc/hexane, m.p. 157–159° C. IR(KBr) 1696, 1604, 1594, 1397, 1344, 1308, 1210, 1168, 1118, 1081, 999, 816, 750, 631 cm$^{-1}$. UV (CH$_2$Cl$_2$): λ$_{max}$=287 nm (ε=33.1×10$^3$) $^1$H-NMR (CDCl$_3$): δ4.75 (s, 2H), 6.25 (t, 1H, J=60 Hz), 7.77 (d, 2H), 7.89 (d, 2H), 8.10 (2 d, 4H). $^{13}$C-NMR (DMSO-d$_6$): δ47.6, 114.7 (t, J$_{CF}$=283 Hz), 191.3 ppm. $^{19}$F-NMR (CDCl$_3$): δ–121.6 ppm (d, J$_{HF}$=53 Hz). Mass spectrum m/z=344 (M$^+$), 295 (M$^+$—CH$_2$Cl, base peak), 245, 229, 180, 165, 152 amu.

EXAMPLE 41

α-(chloromethyl)-4'-[(difluoromethyl)sulfonyl][1,1'-biphenyl]-4-methanol

To a 500-mL sidearm flask equipped with a thermometer and nitrogen inlet was charged 47.0 g (0.130 mol) of ca. 95%-pure 2-chloro-1-[4'-[(difluoromethyl) -sulfonyl][1,1'-biphenyl]-4-yl]ethanone, 200 mL of tetrahydrofuran, 1.40 mL (23 mmol) of glacial acetic acid, and 10 mL of water. The orange solution was cooled to 5° C. and 2.4 g (31 mmol) of sodium borohydride was added in three portions over about 15 minutes. The mixture was held for 15 minutes at 10° C., diluted with 200 mL of water, and acidified to pH 2 with about 40 mL of aqueous 1N HCl. Most of the THF was removed in vacuo and the oil was extracted with 400 mL of ethyl acetate. The ethyl acetate layer was washed in succession with water, aqueous NaHCO$_3$, and aqueous NaCl, then dried with MgSO$_4$, filtered, and concentrated to dryness. Then residue was crystallized from 200 mL of 1:1 toluene/hexanes, filtered, and washed with 50 mL of 1:1 toluene/hexanes to afford 35.3 g (78% yield) of product as a pale orange solid, m.p. 104–107° C.; a sample purified by chromatography and crystallization from EtOAc/hexanes had m.p. 111–112° C. $^1$H-NMR (CDCl$_3$) δ3.3 (br s, 1H), 3.7 (dd, 1H), 3.8 (dd, 1H), 5.0 (dd, 1H), 6.23 (t, 1H, J=60 Hz), 7.55 (d, 2H), 7.65 (d, 2H), 7.82 (d, 2H), 8.05 (d, 2H). $^{13}$C-NMR (CDCl$_3$) δ50.5, 73.5, 114.7 (t, J$_{CF}$=286 Hz), 126.9, 127.7, 128.1, 130.1, 131.1, 138.6, 141.0, 148.1 ppm. $^{19}$F-NMR (CDCl$_3$) δ–121.8 ppm (d, J$_{HF}$=53 Hz). Mass spectrum m/z=346 (M$^+$), 297 (M$^+$—CH$_2$Cl, base peak), 182 amu.

EXAMPLE 42

N-[2-chloro-1-[4'-[(difluoromethyl)sulfonyl]-[1,1'-biphenyl]-4-yl]ethyl]-2,6-difluorobenzamide To a 100-mL sidearm flask with magnetic stirrer was charged 13.9 g (0.100 mol) of 2,6-difluorobenzonitrile and 20 mL of dichloromethane. The solution was cooled to 5° C. with good stirring and 4.2 mL (8.0 g, 80 mmol) of concentrated sulfuric acid was added, followed by of 10.0 g (28.9 mmol) of α-(chloromethyl)-4'-[(difluoromethyl) -sulfonyl] [1,1'-biphenyl]-4-methanol as a solid, maintaining the temperature at 5–10° C. After 1 h stirring at 10° C., the mixture was poured onto 50 g of ice with stirring. Approximately 10 mL of 28% aqueous ammonia was added to neutralize the acid, dichloromethane was removed in vacuo, 80 mL of cyclohexane was added, and the mixture was filtered, washed with water, then with cyclohexane, and suction-dried overnight to afford ca. 12 g (86%) of product, m.p. 143–149° C. An analytical sample was prepared by recrystallization from isopropanol, m.p. 153–155° C. IR (KBr): 1660, 1626, 1593, 1521, 1467, 1344, 1308, 1161, 1080, 823 cm$^{-1}$. UV (CH$_2$Cl$_2$): λ$_{max}$=276 nm (ε=24.8×10$^3$). $^1$H-NMR (CDCl$_3$): δ4.02 (d of q, 2H), 5.68 (m, 1H), 6.22 (t, 1H, J=53 Hz), 6.7 (br d, 1H,), 7.0 (t, 2H, J=9 Hz), 7.41 (m, 1H), 7.53 (d, 2H), 7.65 (d, 2H), 7.83 (d, 2H), 8.05, (d, 2H). $^{13}$C-NMR (CDCl$_3$): δ47.4, 53.8, 112.1 (dd, J$_{CF}$=2, 23 Hz), 113.4 (t, J$_{CF}$=7 Hz), 114.5 (t, J$_{CF}$=286 Hz), 127.3, 127.6, 127.9, 130.2, 131.0, 132.0 (t, J$_{CF}$=10 Hz), 138.4, 138.8, 147.9, 159.8, 160.0 (dd, J$_{CF}$=7,253 Hz). $^{19}$F-NMR (CDCl$_3$) δ–112.1 (t, J$_{HF}$=7.3 Hz), –121.8 (d, J$_{HF}$=53 Hz).

EXAMPLE 43

4-[4'-[(difluoromethyl)sulfonyl][1,1'-biphenyl]-4-yl]-2-(2,6-difluorophenyl)-4,5-dihydrooxazole To a slurry of 9.18 g (18.9 mmol) of N-[2-chloro-1-[4'-[(difluoromethyl) -sulfonyl][1,1'-biphenyl]-4-yl]ethyl]-2,6-difluorobenzamide in 70 mL of isopropanol was added a solution of 1.8 g (22.5 mmol) of aqueous 50% NaOH at 25–30° C. The mixture was allowed to stir for 30 minutes at ambient temperature, diluted with 40 mL of water, and filtered. The solid product was washed with 20 mL of 50% aqueous isopropanol and suction-dried to afford 7.5 g (88%) of 4-[4'-[(difluoromethyl)sulfonyl][1,1'-biphenyl]-4-yl]-2-(2,6-difluorophenyl)-4,5-dihydrooxazole, m.p. 107–111° C. An analytical sample was prepared by recrystallization from isopropanol, m.p. 109–111° C. IR(KBr): 1669, 1622, 1593, 1485, 1469, 1395, 1345, 1300, 1285, 1240, 1168, 1161, 1114, 1081, 1053, 1041, 1012, 822, 793 cm$^{-1}$. UV(CH$_2$Cl$_2$): λ$_{max}$=279 nm (ε=25.9×10$^3$). $^1$H-NMR (benzene-d$_6$): δ3.9 (t, 1H), 4.25 (dd, 1H), 5.15 (dd, 1H), (dq, 2H), 5.68 (m, 1H), 6.22 (t, 1H, J=53 Hz), 6.7 (br d, 1H), 7.0 (t, 2H, J=9 Hz), 7.41 (m, 1H), 7.53 (d, 2H), 7.65 (d, 2H), 7.83 (d, 2H), 8.05 (d, 2H). $^{13}$C-NMR (CDCl$_3$): δ69.9, 74.6, 107.1 (dd, J$_{CF}$=2, 23 Hz), 114.8, 127.6, 127.9, 128.1, 131.2, 132.2. $^{19}$F-NMR (CDCl$_3$): δ–112.1 (t, J$_{HF}$=7.3 Hz), –121.8 (d, J$_{HF}$=53 Hz).

What is claimed is:

1. A compound having Formula I:

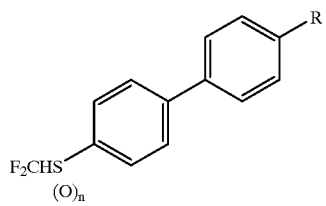

wherein

R is selected from H, —C(O)CH$_2$R$^4$, —CH(OH)CH$_2$R$^4$, —CH(NH$_2$)CH$_2$R$^4$ and

and salts thereof;

R$^4$ is OC(O)Ar, Cl, or Br;

R$^5$ is OH, Cl, Br, or OSO$_2$A;

A is methyl, phenyl or p-tolyl;

Ar is 2,6-difluorophenyl, 2-chlorophenyl or 2-chloro-6-fluorophenyl;

n is 1 or 2; and

* denotes a stereogenic center.

2. A compound according to claim 1 wherein R is:

3. A composition comprising a mixture of compounds according to claim 1, having the stereogenic center designated by *, which compounds are enantiomerically enriched in the S configuration.

4. A process for preparing a racemic or enantiomerically enriched arthropodicidal oxazoline of Formula II:

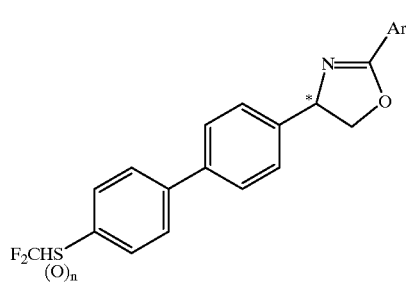

wherein

Ar is 2,6-difluorophenyl, 2-chlorophenyl or 2-chloro-6-fluorophenyl;

n is 1 or 2; and

* denotes a stereogenic center;

comprising cyclizing a compound of Formula III:

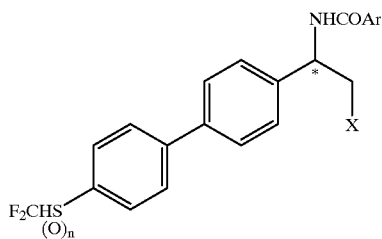

wherein

X is Cl, Br or OSO$_2$A;

A is methyl, phenyl or p-tolyl.

5. A process according to claim 4 comprising the additional step of preparing a compound of Formula III by reacting a compound of Formula IV:

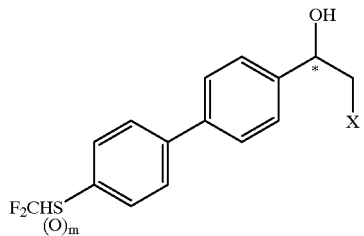

where m is 0, 1 or 2 with ArCN provided that when m is 0 an oxidation is performed to provide the compounds where n is 1 or 2.

6. A process according to claim 5 comprising the additional step of preparing the compound of Formula V:

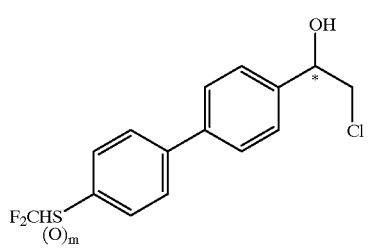

by reducing a compound of Formula VI:

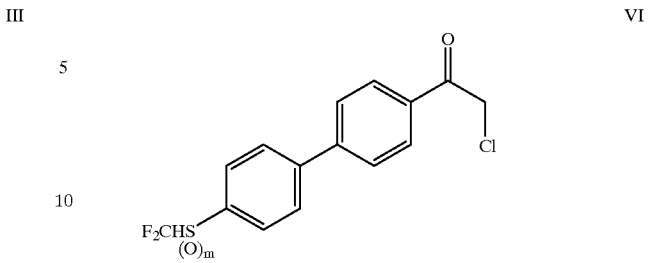

7. A process according to claim 6 comprising the additional step of preparing the compound of Formula VI wherein m is 1 or 2, by reacting a compound of Formula VII:

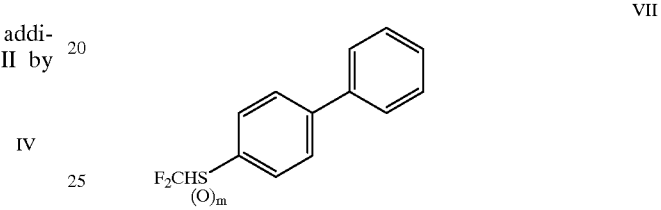

with ClCH$_2$C(O)Cl in the presence of aluminum trichloride.

8. A process according to claim 4 comprising the additional step of preparing a compound of Formula III wherein X is Cl, comprising reacting a compound of Formula VII with a compound selected from compounds of the formula ArC(O)NHCH=CHCl, ArC(O)NHCHOHCH$_2$Cl and ArC(O)NHCH(CH$_2$Cl)OCH(CH$_2$Cl)NHC(O)Ar and mixtures thereof.

9. A compound having the formula selected from ArC(O)NHCH=CHCl, ArC(O)NHCHOHCH$_2$Cl and ArC(O)NHCH(CH$_2$Cl)OCH(CH$_2$Cl)NHC(O)Ar wherein Ar is 2,6-difluorophenyl, 2-chlorophenyl or 2-chloro-6-fluorophenyl.

10. A compound according to claim 9 having Formula VIII:

ArC(O)NHCH(CH$_2$Cl)OCH(CH$_2$Cl)NHC(O)Ar     VII wherein Ar is 2,6-difluorophenyl.

11. A process for preparing a compound according to claim 9 by reaction of an amide of Formula IX:

ArCONH$_2$     IX with chloroacetaldehyde in the presence of a catalyst in a solvent.

* * * * *

UNITED STATES PATENT AND TRADEMARK OFFICE
CERTIFICATE OF CORRECTION

PATENT NO. : 6,063,932
DATED : May 16, 2000
INVENTOR(S) : Gary David Annis, Rafael Shapiro It is certified that error appears in the above-identified patent and that said Letters Patent is hereby corrected as shown below:

Column 7,
Scheme C1, in Structure 11, the bond linking the oxygen to the rest of the molecule should be a double bond as shown in the structure below.

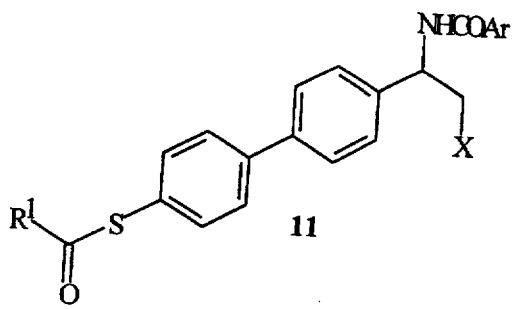

Column 16,
Line 45, "biphenyl4-ol" should read -- biphenyl-4-ol --.

Column 18,
Equation 18, in Formula 25, the extra methylene between $CO_2R^7$ and the rest of the molecule should be removed as shown in the structure below.

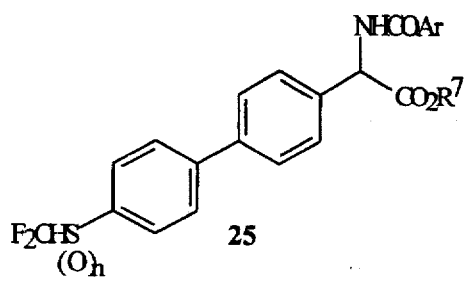

UNITED STATES PATENT AND TRADEMARK OFFICE
CERTIFICATE OF CORRECTION

PATENT NO. : 6,063,932
DATED : May 16, 2000
INVENTOR(S) : Gary David Annis, Rafael Shapiro It is certified that error appears in the above-identified patent and that said Letters Patent is hereby corrected as shown below:

<u>Column 20,</u>
Equation 23, the substituent on Formula 29 "CIS(O)$_2$" should read -- CIS(O)$_2$ --.

Signed and Sealed this

Twenty-seventh Day of November, 2001

Attest:

*Attesting Officer*

NICHOLAS P. GODICI
*Acting Director of the United States Patent and Trademark Office*